US006905817B1

(12) United States Patent
Titievsky et al.

(10) Patent No.: US 6,905,817 B1
(45) Date of Patent: Jun. 14, 2005

(54) RET-INDEPENDENT SIGNALING PATHWAY FOR GDNF

(75) Inventors: Alexey Vladimirovich Titievsky, Helsinki (FI); Dmitri Poteriaev, Helsinki (FI); Urmas Arumäe, Espoo (FI); Mart Saarma, Helsinki (FI)

(73) Assignee: Licestia Ltd., Helsinki (FI)

( * ) Notice: Subject to any disclaimer, the term of this patent is extended or adjusted under 35 U.S.C. 154(b) by 0 days.

(21) Appl. No.: 09/410,319

(22) Filed: Oct. 1, 1999

Related U.S. Application Data

(60) Provisional application No. 60/102,647, filed on Oct. 1, 1998.

(51) Int. Cl.$^7$ .......................... C12Q 1/68; C12N 15/00; C12N 15/63; C12N 1/20; C07H 21/04
(52) U.S. Cl. .................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .................... 435/6, 91.1, 91.2; 536/24.3; 935/6; 436/518

(56) References Cited

U.S. PATENT DOCUMENTS 5,981,194 A * 11/1999 Jefferies et al. .............. 435/7.1

FOREIGN PATENT DOCUMENTS

| WO | WO 97/18240 | 5/1997 |
|---|---|---|
| WO | WO 98/36072 | 8/1998 |

OTHER PUBLICATIONS

Shen et al., "Correlations among tyrosine phosphorylation of Shc, p72 syk, PLC-gamma1, and Ca2 + flux in Fcgam-maRIIA signalling", *Journal of Immunology*, vol. 152, pp. 3017-3023.*

Chalazonitis et al., "Age dependent differences in the effects of GDNF—", *Development Biology*, vol. 204, pp. 385-406, 1998.*

Airaksinen, M.S. et al., "GDNF family neurotrophic factor signaling: four masters, one servant?" *Mol. Cell. Neurosci.*, 1999, 13, 313-325.

Arénas, E. et al., "GDNF prevents degeneration and promotes the phenotype of brain noradrenergic neurons in vivo," *Neuron*, 1995, 15, 1465-1473.

Baloh, R.H. et al., "Artemin, a novel member of the GDNF ligand family, supports peripheral and central neurons and signals through the GFRα3-RET receptor complex," *Neuron*, 1998, 21, 1291-1302.

Beck, K.D. et al., "Mesencephalic dopaminergic neurons protected by GDNF from axotomy-induced degeneration in the adult brain," *Nature*, 1995, 373, 339-341.

Berridge, M.J., "Neuronal calcium signaling," *Neuron*, 1998, 21, 13-26.

Borrello, M.G. et al., "The full oncogenic activity of Ret/ptc2 depends on tyrosine 539, a docking site for phospholipase Cgamma," *Mol. Cell Biol.*, 1996, 16, 2151-2163.

Bourette, R.P. et al., "Sequential activation of phoshatidylinositol 3-kinase and phospholipase C-gamma2 by the M-CSF receptor is necessary for differentiation signaling," *EMBO J.*, 1997, 16, 5880-5893.

Brown, D.A. et al., "Functions of lipid rafts in biological membranes," *Ann. Rev. Cell Developmental Biol.*, 1998, 14, 111-136.

Buj-Bello, A. et al., "GDNF is an age-specific survival factor for sensory and autonomic neurons," *Neuron*, 1995, 15, 821-828.

Buj-Bello, A. et al., "Neurturin responsiveness requires a GPI-anchored receptor and the Ret receptor tyrosine kinase," *Nature*, 1997, 387, 721-724.

Cacalano, G. et al., "GFRα1 is an essential receptor component for GDNF in the developing nervous system and kidney," *Neuron*, 1998, 21, 53-62.

Chiariello, M. et al., "Signaling of the Ret receptor tyrosine kinase through the c-Jun $NH_2$-terminal protein kinases (JNKS): evidence for a divergence of the ERKs and JNKs pathways induced by Ret," *Oncogene*, 1998, 16, 2435-2445.

Davletov, B.A. et al., "Vesicle exocytosis stimulated by alpha-latrotoxin is mediated by latrophilin and requires both external and stored $Ca^{2+}$," *EMBO J.*, 1998, 17, 3909-3920.

Dikic, I. et al., "A role for Pyk2 and Src in linking G-protein-coupled receptors with MAP kinase activation," *Nature*, 1996, 383, 547-550.

Durbec, P. et al., "GDNF signaling through the Ret receptor tyrosine kinase," *Nature*, 1996, 381, 789-793.

Enomoto, H. et al., "GFR alphal-deficient mice have deficits in the enteric nervous system and kidneys," *Neuron*, 1998, 21, 317-324.

Finkbeiner, S. et al., "CREB: A major mediator of neuronal neurotrophin responses," *Neuron*, 1997, 19, 1031-1047.

Finkbeiner, S. et al., "$Ca^{2+}$ channel-regulated neuronal gene expression," *J. Neurobiology*, 1998, 37, 171-189.

Friedrichson, T. et al., "Microdomains of GPI-anchored proteins in living cells revealed by crosslinking," *Nature*, 1998, 394, 802-805.

Fukunaga, K. et al., "Role of MAP kinase in neurons," *Mol. Neurobilogy*, 1998, 16, 79-95.

Ghosh, A. et al., "Calcium signaling in neurons: molecular mechanisms and cellular consequences," *Science*, 1995, 268, 239-247.

(Continued)

Primary Examiner—Jeffrey Fredman
Assistant Examiner—Arun Chakrabarti
(74) Attorney, Agent, or Firm—Woodcock Washburn LLP

(57) ABSTRACT

Methods for screening for agonists and antagonists of GPI-anchored independent intracellular signaling resulting in $[Ca^{2+}]_i$ elevation, ERK1, ERK2 and CREB phosphorylation, and Src family kinase activation are described, as well as methods for treatment involving administration of agonists/antagonists of such signaling.

91 Claims, 11 Drawing Sheets

OTHER PUBLICATIONS

Golden, J.P. et al., "Expression of neurturin, GDNF, and GDNF family–receptor mRNA in the developing and mature mouse," *Experimental Neurology*, 1999, 58, 504–528.

Green, J.M. et al., "Role for a glycan phosphoinositol anchor in (Fed. Cir. gamma receptor synergy," *J. Cell Biology*, 1997, 139, 1209–1217.

Harder, T. et al., "Lipid domain structure of the plasma membrane revealed by patching of membrane components," *J. Cell Biology*, 1998, 141, 929–942.

Henderson, C.E. et al., "GDNF: a potent survival factor for motoneurons present in peripheral nerve and muscle," *Science*, 1994, 266, 1062–1064.

Hishiki, T. et al., "Glial cell line–derived neurotrophic factor/neurturin–induced differentiation and its enhancement by retinoic acid in primary human neuroblastomas expressing c–Ret, GFR alpha–1, and GFR alpha–2," *Cancer Res.*, 1998, 58, 2158–2165.

Impey, S. et al., "Making new connections: role of ERK/MAP kinase signaling in neuronal plasticity," *Neuron*, 1999, 23, 11–14.

Jiang, H. et al., "Actions of the neurotrophins on calcium uptake," *J. Neuroscience Res.*, 1997, 50, 355–360.

Jing, S.Q. et al., "GDNF–induced activation of the Ret protein tyrosine kinase is mediated by GDNFR–alpha, a novel receptor for GDNF," *Cell*, 1996, 85, 1112–1124.

Jing, S. et al., "GFRα–2 and GFRα–3 are two new receptors for ligands of the GDNF family," *J. Biol. Chem.*, 1997, 272, 33111–33117.

Khare, S. et al., "1,25 dihydroxyvitamin D3 stimulates phospholipase C–gamma in rat colonocytes: role of c–Src in PLC–gamma activation," *J. Clin. Invest.*, 1997, 99, 1831–1841.

Klein, R.D. et al., "A GPI–linked protein that interacts with Ret to form a candidate neurturin receptor," *Nature*, 1997, 387, 717–721.

Kokaia, Z. et al., "GDNF family ligands and receptors are differentially regulated after brain insults in the rat," *Eur. J. Neurosci.*, 1999, 11, 1202–1216.

Kotzbauer, P.T. et al., "Neurturin, a relative of glial––cell–line–derived neurotrophic factor," *Nature*, 1996, 384, 467–470.

Lang, D.M. et al., "Identification of reggie–1 and reggie–2 as plasmamembrane–associated proteins which cocluster with activated GPI–anchored cell adhesion molecules in non–caveolar micropatches in neurons," *J. Neurobiology*, 1998, 37, 502–523.

Lin, L.F. et al., "GDNF: a glial cell line–derived neurotrophic factor for midbrain dopaminergic neurons," *Science*, 1993, 260, 1130–1132.

Luttrell, L.M. et al., "Role of c–Src tyrosine kinase in G protein–coupled receptor– and Gbetagamma subunit–mediated activation of mitogen–activated protein kinases," *J. Biol. Chem.*, 1996, 271, 19443–19450.

Luttrell, L.M. et al., "G protein–coupled receptors mediate two funcionally distinct pathways of tyrosine phosphorylation in rat la fibroblasts. Shc phosphorylation and receptor endocytosis correlate with activation of Erk kinases," *J. Biol. Chem.*, 1997, 272 31648–31656.

Luttrell, L.M. et al., "β–arrestin–dependent formation of β$_2$ adrenergic receptor–Src protein kinase complexes," *Science*, 1999, 283, 655–661.

Meyer zu Heringdorf D. et al., "Sphingosine kinase–mediated Ca$^{2+}$ signaling by G–protein–coupled receptors," *EMBO J.*, 1998, 17, 2830–2837.

Milbrandt, J. et al., "Persephin, a novel neurotrophic factor related to GDNF and neurturin," *Neuron*, 1998, 20, 245–253.

Moore, M.W. et al., "Renal and neuronal abnormalities in mice lacking GDNF,"*Nature*, 1996, 382, 76–79.

Natarajan, D. et al., "Multipotential progenitors of the mammalian enteric nervous system capable of colonising aganglionic bowel in organ culture," *Development*, 1999, 126, 157–168.

Oppenheim, R.W. et al., "Developing motor neurons rescued from programmed and axotomy– induced cell death by GDNF," *Nature*, 1995, 373, 344–346.

Pichel, J.G. et al., "Defects in enteric innervation and kidney development in mice lacking GDNF," *Nature*, 1996, 382, 73–76.

Pirvola, U. et al., "Glial cell line–derived neurotrophic factor (GDNF), is a potent trophic factor in the postnatal rat cochlea," 1996, Abstract No. 572, 1 page.

Poteryaev, D., et al., "GDNF triggers a novel ret–independent Src kinase family–coupled signaling via a GPI–linked GDNF receptor α1," *FEBS Letters*, 1999, 463, 63–66.

Rossi, J. et al., "Retarded growth and deficits in the enteric and parasympathetic nervous system in mice lacking GFRα2, a functional neurturin receptor," *Neuron*, 1999, 22, 243–252.

Saarma, M. et al., "Other neurotrophic factors: glial cell line–derived neurotrophic factor (GDNF)," *Microscopy Res. Techniques*, 1999, 45, 292–302.

Sanicola, M. et al., "Glial cell line–derived neurotrophic factor–dependent RET activation can be mediated by two different cell–suface accessory proteins,"*Proc. Nat. Acad. Sci. USA*, 1997, 94, 6238–6243.

Sánchez, M.P. et al., "Renal agenesis and the absence of enteric neurons in mice lacking GDNF," *Nature*, 1996, 382, 70–73.

Sargiacomo, M. et al., "Signal transducing molecules and glycosyl–phosphatidylinositol–linked proteins form a caveolin–rich insoluble complex in MDCK cells," *J. Cell Biol.*, 1993, 122, 789–807.

Schuchardt, A. et al., "Defects in the kidney and enteric nervous system of mice lacking the tyrosine kinase receptor Ret," *Nature*, 1994, 367, 380–383.

Sharenberg, A.M. et al., "PtdIns–3,4,5–P3: a regulatory nexus between tyrosine kinases and sustained calcium signals," *Cell*, 1998, 94, 5–8.

Simons, K. et al., "Functional rafts in cell membranes," *Nature*, 1997, 387, 569–572.

Stam, J.C. et al., "Invasion of T–lymphoma cells: cooperation between Rho family GTPases and lysophospholipid receptor signaling," *EMBO J.*, 1998, 17, 4066–74.

Suvanto, P. et al., "Cloning, mRNA distribution and chromosomal localisation of the gene for glial cell line–derived neurotrohic factor receptor β, a homologue to GDNFR–α," *Human Mol. Genetics*, 1997, 6, 1267–1273.

Takei, K. et al., "Regulation of nerve growth mediated by inositol 1,4,5–trisphosphate receptors in growth cones," *Science*, 1998, 282, 1705–1708.

Taraviras, S. et al., "Signaling by the RET receptor tyrosine kinase and its role in the development of the mammmalian enteric nervous system," *Development*, 1999, 126, 2785–2797.

Thomas, S.M. et al., "Cellular functions regulated by Src family kinases," *Ann. Rev. Cell & Developmental Biol.*, 1997, 13, 513–609.

Thorn, P. et al., "Local and global cytosolic $Ca^{2+}$ oscillations in exocrine cells evoked by agonists and inositol trisphosphate," *Cell*, 1993, 74, 661–668.

Tomac, A. et al., "Protection and repair of the nigrostriatal dopaminergic system by GDNF in vivo," *Nature*, 1995, 373, 335–339.

Treanor, J.J. et al., "Characterization of a multicomponent receptor for GDNF," *Nature*, 1996, 382, 80–83.

Trupp, M. et al., "Peripheral expression and biological activities of GDNF, a new neurotrophic factor for avian and mammalian peripheral neurons," *J. Cell Biol.*, 1995, 130, 137–148.

Trupp, M. et al., "Functional receptor for GDNF encoded by the c–ret proto–oncogene," *Nature*, 1996, 381, 785–788.

Trupp, M. et al., "Complementary and overlapping expression of glial cell line–derived neurotrophic factor (GDNF), c–Ret proto–oncogene, and GDNF receptor–alpha indicates multiple mechanisms of trophic actions in the adult rat CNS," *J. Neuroscience*, 1997, 17, 3554–3567.

Trupp, M. et al., "Ret–dependent and –independent mechanisms of glial cell line–derived neurotrophic factor signaling in neuronal cells," *J. Biol. Chem.*, 1999, 274, 20885–20894.

Usachev, Y.M. et al., "$Ca^{2+}$ influx in resting rat sensory neurones that regulates and is regulated by ryanodine–sensitive $Ca^{2+}$ stores," *J. Physiology*, 1999, 519, 115–130.

Varma, R. et al., "GPI–anchored proteins are organized in submicron domains at the cell surface," *Nature*, 1998, 394, 798–801.

Viola, A. et al., "T lymphocyte costimulation mediated by reorganization of membrane microdomains," *Science*, 1999, 283, 680–682.

Yan, Q. et al., "In vivo neurotrophic effects of GDNF on neonatal and adult facial motor neurons," *Nature*, 1995, 373, 341–344.

Ylikoski, J. et al., "Guinea pig auditory neurons are protected by glial cell line–derived growth factor from degeneration after noise trauma," *Hearing Res.*, 1998, 1–10.

Yu, T. et al., "Expression of GDNF family receptor components during development: implications in the mechanisms of interaction," *J. Neurosci.*, 1998, 18, 4684–4696.

Baloh et al. "GFRalpha3 is an orphan member of the GDNF/neurturin/persephin receptor family", *Proc. Natl.acad.Sci.(USA)*, vol. 95, pp. 5801–5806, 1998.*

* cited by examiner

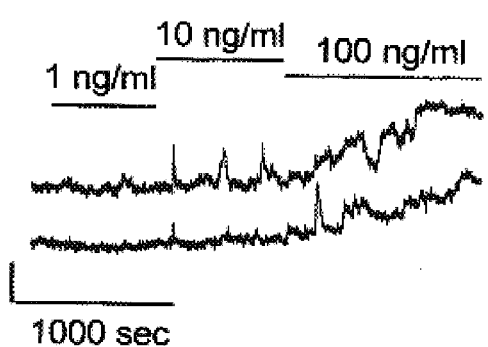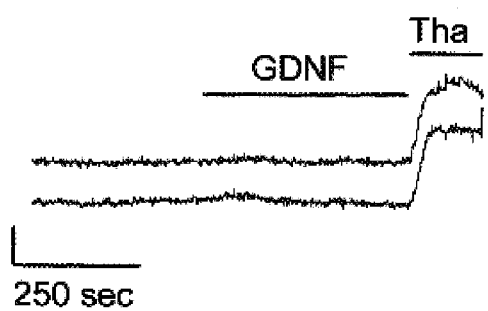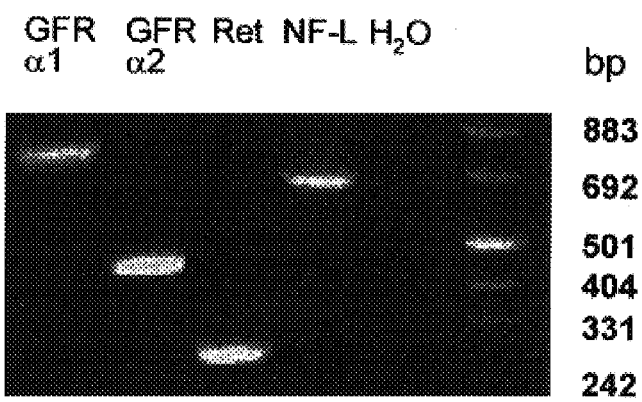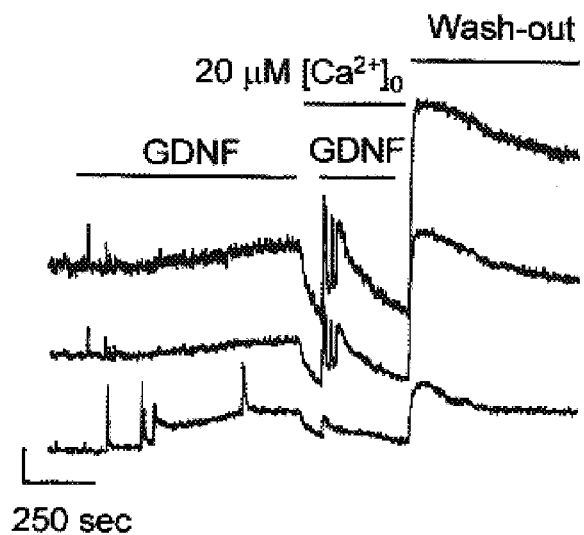

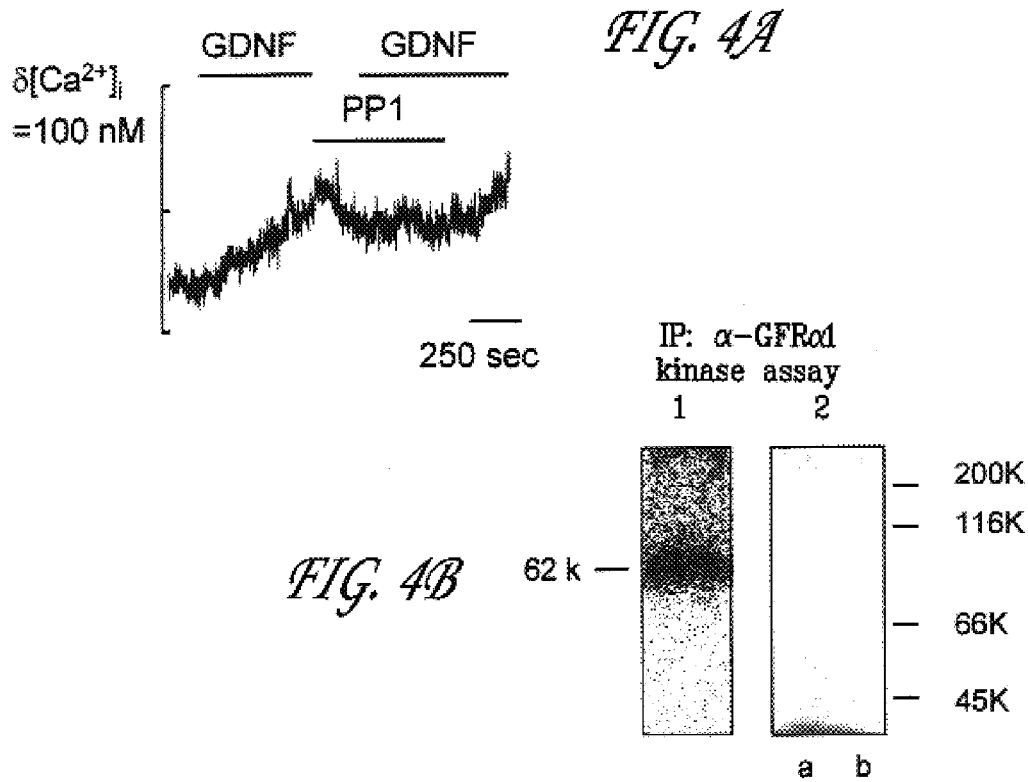
FIG. 4A
FIG. 4B
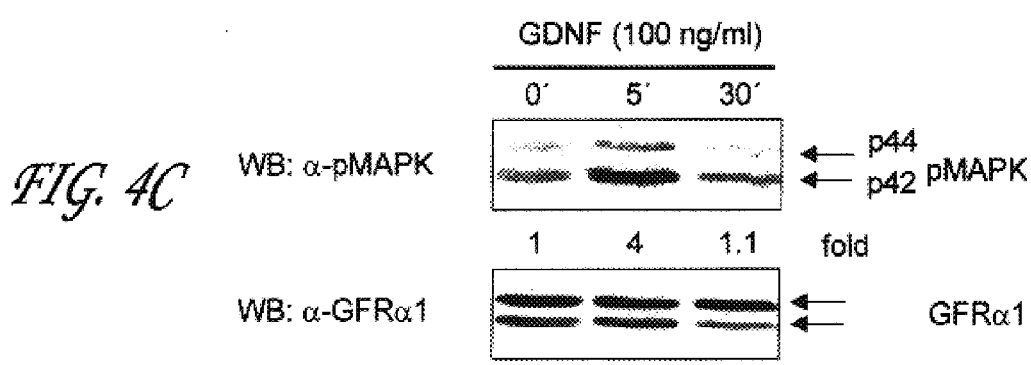
FIG. 4C
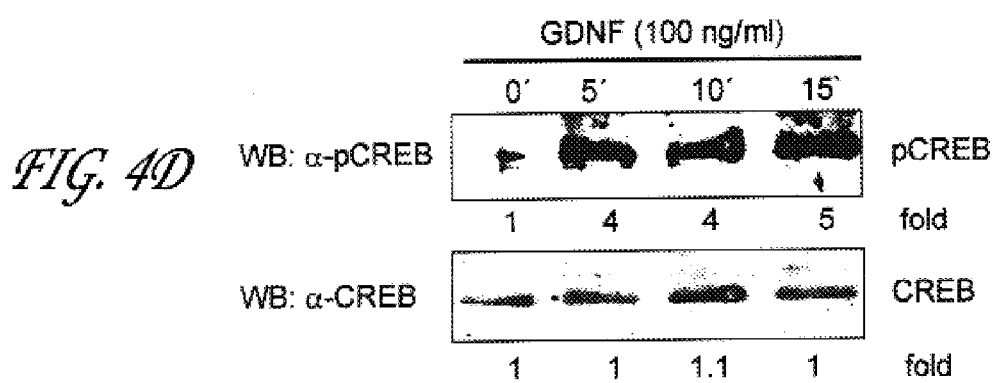
FIG. 4D

SEQUENCE LISTING

```
<160> NUMBER OF SEQ ID NOS:   6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
gcggcaccat gttcctagcc                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
```

```
                                    -continued cagactcagg cagttgggcc                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 3
tattggagca tccatctggg                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 4
agcagttggg cttctccttg                                                    20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
atgaaagggt actgaccatg g                                                  21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
aggaccacac atcactttga g                                                  21
```

RET-INDEPENDENT SIGNALING PATHWAY FOR GDNF

REFERENCE TO RELATED APPLICATIONS

This application claims priority under 35 U.S.C. § 119(e) to U.S. provisional application 60/102,647 filed Oct. 1, 1998, incorporated herein by reference in its entirety.

FIELD OF THE INVENTION

The present invention relates to methods for screening for agonists and antagonists of Ret-independent intracellular signaling.

BACKGROUND OF THE INVENTION

Glial cell line—derived neurotrophic factor (GDNF) (Lin et al., 1993), neurturin (NTN) (Kotzbauer et al., 1996), persephin (PSP) (Milbrandt et al., 1998) and a recently discovered artemin (ART) (Baloh et al., 1998) form a group of TGF-β family-related neurotrphic proteins. Studies in primary neuronal cultures, as well as in lesioned animal models, have provided evidence that GDNF is a survival factor for embryonic midbrain dopaminergic neurons (Beck et al., 1995; Lin et al., 1993, Tomac et al., 1995), spinal motor neurons (Henderson et al., 1994; Oppenheim et al., 1995; Yan et al., 1995), locus coeruleus noradrenergic neurons (Arenas et al., 1995), and subpopulations of peripheral sensory, sympathetic, and parasympathetic neurons (Buj-Bello et al., 1995; Trupp et al., 1995; reviewed by Airaksinen et al., 1999 and Saarma & Sariola, 1999). The pattern of neurotrophic activity of GDNF is therefore promising for its potential use in the treatment of Parkinson disease, Alzheimer disease, motoneuron diseases and several other neurodegenerative diseases. The biological importance of the GDNF family is illustrated by the phenotype of GDNF null mice which display deficits in primary sensory, sympathetic and motor neurons. These mice also fail to develop kidneys and most of the enteric nervous system and they die at birth (Moore et al., 1996; Pichel et al., 1996; Sanchez et al., 1996).

Despite the potential clinical importance of the GDNF receptor family, the intracellular mechanism of GDNF's action is far from understood. Generally GDNF has been thought to act through a multi-component receptor system including a glycosyl-phosphatidyl-inositol (GPI)-anchored GDNF family receptor α1 (GFRα1) (Jing et al., 1996; Treanor et al., 1996) and a transmembrane receptor tyrosine kinase, Ret (Durbec et al., 1996; Trupp et al., 1996). GFRα1, lacking an intracellular domain, has originally been assessed as a binding site for GDNF, serving only in the presentation of the GFRα1/GDNF complex to Ret (Jing et al., 1996; Treanor et al., 1996; Trupp et al., 1997). There is no doubt that the Ret and GPI-anchored GFRα1 are necessary receptors for GDNF (Cacalano et al., 1998, Enomoto et al., 1998) since mice lacking Ret, GDNF or GFRα1 all share a similar phenotype and die soon after birth. However, it is not known whether these GFRα proteins can evoke intracellular signals upon the action of GDNF family proteins in the absence of Ret.

Ret and GFRα1 expression patterns, although similar, exhibit differences in many tissues (Trupp et al., 1997; Enomoto et al., 1998, Golden et al., 1999, Kokaia et al., 1999), which may be a sign of the distinct signaling from GFRα receptors alone or in conjunction with Ret tyrosine kinase in trans (Yu et al., 1998). We recently showed both in vitro and in vivo (Ylikoski et al., 1998), for example, that GDNF promotes survival of postnatal cochlear sensory neurons expressing GFRα1 mRNA but lacking Ret mRNA. This difference in expression patterns may be a sign of distinct Ret-independent signaling triggered by activation of GFRα receptors.

The triggering of GDNF-dependent intracellular signaling in RN33B cells has also been described (PCT/US96/18197, incorporated herein by reference). RN33B cells were described therein as expressing four putative receptors for GDNF, none of which was c-Ret. Two of the receptors were later determined to be GFRα1 and GFRα2 (reported as GDNFRα and GDNFRβ, respectively, U.S. patent application Ser. No. 08/861,990, incorporated herein by reference). The mechanism of the Ret-independent signaling, however, was not known or described.

Although GPI-anchored membrane proteins have not been conclusively shown to exhibit independent intracellular signaling functions, evidence suggesting this possibility has been increasing (Simons and Ikonen, 1997; Friedrichson and Kurzchalia, 1998; Harder et al., 1998; Varma and Mayor, 1998; Viola et al., 1999). It has been shown, for example, that GPI-anchored: proteins in the immune system can mediate intracellular signaling events, such as activation of the small G-proteins, Src-type tyrosine kinases and elevation of intracellular free calcium concentration ($[Ca^{2+}]_i$) (Green et al., 1997; Brown and London, 1998; Viola et al., 1999). GPI-anchored independent signaling has not previously been shown in cells of the nervous system, however.

The aim of the invention, therefore, is to further elucidate Ret independent intracellular signaling. We specifically address the role of GDNF-activated signaling in dorsal root ganglion (DRG) neurons isolated from Ret-null ($Ret^{-/-}$) transgenic mice (Schuchardt et al., 1994) and in other Ret-negative cell lines, for the purpose of developing a method for identifying compounds which are agonists or antagonists of Ret independent signaling.

SUMMARY OF THE INVENTION

The present invention provides methods for screening for compounds that are agonists or antagonists of GPI-anchored receptor mediated intracellular signaling, more specifically, GFRα1-dependent, Ret-independent intracellular signaling, and methods for preventing and treating neuronal diseases comprising the use of such compounds.

In one aspect, the present invention relates to methods for identifying compounds which are agonists of intracellular signaling effected by GPI-anchored receptors in nervous system cells comprising incubating nervous system cells having such receptors with a test compound and determining whether intracellular signaling has been effected in the cells.

In another aspect, the present invention relates to methods for identifying compounds which are antagonists of intracellular signaling effected by GPI-anchored receptors in nervous system cells comprising incubating nervous system cells having such receptors with a test compound in the presence of a sufficient amount of an agonist of such signaling, and determining whether such signaling is decreased in the cells, as compared to controls run in the absence of the compound.

In a further aspect, the present invention relates to a method for identifying compounds which are antagonists of GFRα1-dependent, Ret-independent intracellular signaling by incubating cells which express GFRα1 receptors, but not Ret, with a compound to be tested in the presence of a sufficient amount of an agonist of such signaling, and determining whether such signaling is decreased in the cells, as compared to controls run in the absence of the compound.

In still another aspect, the present invention relates to a method for identifying compounds which are agonists of GFRα1-dependent, Ret-independent intracellular signaling by incubating cells which express GFRα1 receptors, but not Ret, with a compound previously determined to bind GFRα1 and determining whether the compound causes an increase in $[Ca^{2+}]_i$.

In a further aspect, the present invention relates to a method for identifying compounds which are antagonists of GFRα1-dependent, Ret-independent intracellular signaling by incubating cells which express GFRα1 receptors, but not Ret, with a compound to be tested in the presence of a sufficient amount of an agonist of GFRα1-dependent, Ret-independent intracellular signaling effective for increasing $[Ca^{2+}]_i$ and determining whether cells incubated with the compound have decreased $[Ca^{2+}]_i$ levels as compared with controls not incubated with the compound.

In yet another aspect, the present invention relates to a method for identifying compounds which are agonists of GFRα1-dependent, Ret-independent intracellular signaling by incubating cells which express GFRα1 receptors, but not Ret, with a compound to be tested, preparing a cell lysate, immunoprecipitating the lysate with anti-GFRα1 antibodies to form an immunoprecipitate, and performing assays to measure kinase phosphorylation on that immunoprecipitate.

In a further aspect, the present invention relates to a method for identifying compounds which are antagonists of GFRα1-dependent, Ret-independent intracellular signaling by incubating cells which express GFRα1 receptors, but not Ret, with a compound to be tested in the presence of a sufficient amount of an agonist of GFRα1-dependent, Ret-independent intracellular signaling to effect said kinase phosphorylation, preparing a cell lysate, immunoprecipitating that lysate with anti-GFRα1 antibodies to form an immunoprecipitate, and performing assays to measure kinase phosphorylation on that immunoprecipitate, then comparing the results to controls run in the absence of the compound to be tested.

In yet a further aspect, the invention relates to a method for identifying agonists of GFRα1-dependent, Ret-independent intracellular signaling by incubating cells which express GPI-anchored GFRα1 receptors, but not Ret, with a compound to be tested and determining whether Src-kinase is activated.

In a still further aspect, the invention relates to a method for identifying antagonists of GFRα1-dependent, Ret-independent intracellular signaling by incubating cells which express GPI-anchored GFRα1 receptors, but not Ret, with a compound to be tested and a sufficient amount of an agonist of GFRα1-dependent, Ret-independent intracellular signaling to activate Src kinase and determining whether incubation with the compound has resulted in less activation of Src kinase as compared to controls not incubated with the compound.

In other aspects, the present invention relates to methods for effecting cellular responses in nervous system cells comprising administering an effective amount of either an agonist or antagonist of GPI-anchored intracellular signaling.

In yet another aspect, the present invention relates to a method for identifying agonists of intracellular signaling effected by GFRα receptors comprising incubating lipid rafts prepared from cells having such receptors with a test compound, and determining whether Src-type kinase is activated In yet a further aspect, the present invention relates to a method for identifying antagonists of intracellular signaling effected by GFRα receptors comprising incubating lipid rafts prepared from cells having such receptors with a test compound in the presence of a sufficient amount of an agonist of GFRα-dependent signaling to activate Src-type kinase, and determining whether Src-type kinase activation is reduced in the presence of the test compound, as compared with controls run without the test compound.

In a further aspect, the present invention relates to methods for treating neuronal diseases comprising the administration of an agent which is an agonist or antagonist of GPI-anchored intracellular signaling.

In further aspects, the present invention relates to methods for treating neuronal diseases comprising the administration of agents which are agonists and/or antagonists of GPI-anchored intracellular signaling.

These and other aspects of the invention will become more apparent from the following detailed description.

BRIEF DESCRIPTION OF THE DRAWINGS

FIGS. 4 A–D depict GDNF activation of GFRα1-associated Src kinases, MAP kinases and CRFB in $Ret^{-/-}$ DRG neurons. A. PP1 (10 μM), specific inhibitor of Src-family tyrosine kinases, reversibly blocked GDNF-evoked long-lasting $[Ca^{2+}]_i$ elevation in $Ret^{-/-}$ DRG neurons. The trace is representative of six recordings. B. Panel 1. Triton X-100 insoluble fraction from the lysates of GDNF (100 ng/ml, 5 min)—stimulated $Ret^{-/-}$ mouse DRG neurons was immunoprecipitated (IP) with anti-GFRα1 antibodies. The immunoprecipitate was subjected to an in vitro kinase assay and revealed a major phosphorylated ~60 kD band. Panel 2. This band was not seen in the control kinase assay performed in $Ret^{-/-}$ DRG neurons either with Protein-A Sepharose alone (a) or with bFGF antibodies instead of GFRα1 antibodies (b). C. A rapid GDNF-induced phosphorylation of p42/p44 MAP kinases (upper panel) in $Ret^{-/-}$ DRG neurons. The numbers below lanes indicate the fold induction of p42 band phosphorylation relative to control. Determination of the optical density of the bands was performed using software TINA. The lower panel shows a reprobing of the same filter with anti-GFRα1 mAb by Western blotting (WB) and demonstrates comparable amounts of GFRα1 protein in all lanes (n=3 independent experiments). D. GDNF induced profound increase in CREB Ser-133 phosphorylation. The numbers below lanes indicate the fold induction of CREB phosphorylation relative to control. The lower panel shows the reprobing of the same filter with anti-CREB antibodies and demonstrate comparable amount of CREB protein in all lanes.

DETAILED DESCRIPTION

Figure 1D:
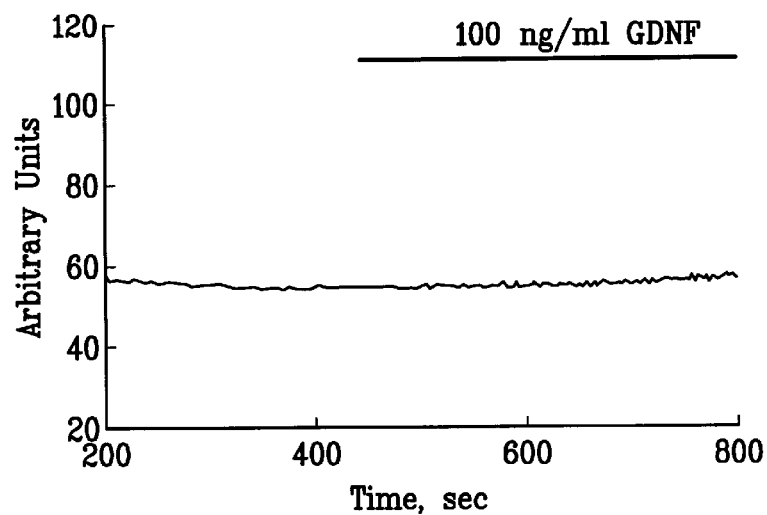
FIGS. 1 A–G depict GDNF-evoked rapid and long-lasting $[Ca^{2+}]_i$ changes in wild type mouse DRG neurons. The vertical bars depict delta$[Ca^{2+}]_i$ changes of 100 nM. A. Neurons were loaded with 10 μM Ca-Green 1AM. Increasing concentrations of 10–100 ng/ml GDNF, applied to the bath as indicated, evoked rapid and long-lasting elevations in $[Ca^{2+}]_i$ (n=15 separate experiments, at least 3–4 neurons recorded in each experiment). B. 100 ng/ml GDNF, heat-inactivated at 98° C. for 15 min did not evoke changes in $[Ca^{2+}]_i$ (8 recorded cells). In these two representative recordings thapsigargin (5 μM) (Tha) was applied at the end of the experiments to prove the functionality of the internal calcium stores. C. RT-PCR shows that wild type DRG neurons express Ret (284 bp fragment), GFRα1 (746 bp fragment), and GFRα2 (429 bp fragment) mRNA. Neurofilament light chain (NF-L, 644 bp fragment) was used as a positive control for neuronal mRNAs. $H_2O$ lane depicts a negative control without added mRNA. The size of molecular weight markers is shown on the right. D. Pre-treatment with 1U/ml PI-PLC eliminates GDNF-evoked $[Ca^{2+}]_i$ elevation. E. Pre-treatment with 5 μM thapsigargin abolished the effect of GDNF. F. Pretreatment with the PLCγ inhibitor U-73122 also resulted in abolishing of the effect of GDNF. G. GDNF (100 ng/ml) evoked both transient and sustained $[Ca^{2+}]_i$ elevation in E18 DRG neurons isolated from GFRα2-negative (GFRα2$^{-/-}$) mice (9 recorded neurons). In these neurons nominal removal of external $Ca^{2+}$ (no added EGTA, about 20 μM free $Ca^{2+}$) led to the rapid decline of $[Ca^{2+}]_i$. In this condition addition of GDNF evoked fast, transient and often oscillatory responses in all of these cells. Re-addition of external $Ca^{2+}$ (wash-out) evoked a rise in $[Ca^{2+}]_i$ in GFRα2 $^{-/-}$ (9 recorded cells) as well as in wild type DRG neurons (8 recorded cells).

An increasing amount of evidence suggests that GPI-linked proteins associated with lipid rafts (Sargiacomo, 1993; Fra et al., 1994; Casey, 1995; Simons & Ikonen, 1997; Xavier et al., 1998) are able to mediate intracellular signaling events in vitro and in vivo (Green et al., 1997; Simons and Ikonen, 1997; Mayor et al., 1998). The existence of microdomains of GPI-anchored proteins was recently shown in living cells (Varma & Mayor, 1998;

Friedrichson & Kurzchalia, 1998). The GFRα1 proteins, as described above, are GPI-anchored.

We disclose herein that GDNF can evoke potent intracellular signaling through a Ret-independent, GPI-anchored GFRα1-mediated pathway. We also disclose tat, upon GDNF binding, GPI-anchored GFRα1 can solely evoke the induction of PLCγ signaling pathway that is dependent on the activation of Src Family kinases and results in the long-lasting sustained $[Ca^{2+}]_i$. We further disclose that in addition to activating PLCγ and calcium signaling, GDNF activates Ret-independent Src kinase-mediated ERK1/ERK2 (MAPK)and CREB in Ret$^{-/-}$ DRG neurons and in the different Ret-negative cell lines.

We further describe assays for compounds that are agonists or antagonists of GPI-anchored intracellular signaling based upon $[Ca^{2+}]_i$ elevation and the activation of Src family kinases. We also disclose methods for identifying compounds that are agonists or antagonists of GPI-anchored intracellular signaling based upon phosphorylation of MAPK and CREB.

Whether a compound binds to GFRα1 can be readily determined by one skilled in the art using, for example, methods for identifying compounds which bind receptors for GDNF as described in U.S. patent application Ser. No. 08/861,990, incorporated herein by reference. Alternatively, the Biacore device (Pharmacia) can be used. Src kinase activity can be determined indirectly by looking at the tyrosine phosphorylation state or kinase activity of its substrates that include, but is not limited to, p130Cas (Sakai et al., 1997) and FAK (Polte et al., 1997). Methods for determining MAPK and CREB activation are described herein.

Activation of the GFRα1-dependent, Ret-independent signaling pathways may stimulate different cellular responses than those of the Ret-dependent pathway. For instance, neuronal survival, neurite extension, enhancement of neurotansmitter synthesis, or other cellular responses to GDNF may be preferentially enhanced by one pathway over the other. Agonists or antagonists of one of these signaling mechanisms may provide for more specific cellular responses than that of GDNF itself and thereby gain therapeutic advantage over GDNF. Methods for identifying agonists and antagonists of Ret-dependent intracellular signaling is described in U.S. patent application Ser. No. 08/861,990, incorporated herein by reference. Methods to develop agonists of both signaling pathways, antagonists of both pathways, agonists or antagonists of just one pathway, or compounds that agonize one pathway but antagonize the other pathway are contemplated herein.

GFRα1-dependent, Ret-independent signaling may promote the survival and function of specific neuronal populations. Auditory neurons, which receive the impulses from the sensory auditory hair cells and transmit them to the brain, respond to GDNF both in vitro and in vivo. GDNF has been shown to protect neurons of the inner ear. (Tay et al., 1998; Shoji et al., 1998; and Keithley et al., 1998.) GFRα1 is expressed on auditory neurons in the absence of Ret. Therefore, a mechanism is described herein that suggests how the Ret-independent signaling works and how this population of neurons may be supported by compounds that specifically mimic GDNF dimerization of GFRα1 at the receptor or at the subsequent intracellular signaling events.

"A", "an", and "the" as used herein refer to the singular and plural.

The term "effect" as used herein means an alteration or change. An effect can be positive, such as causing an increase in some material, or negative, e.g., antagonistic or inhibiting.

The term "agonist" as used herein refers to a compound or composition that can stimulate or positively influence the intracellular signaling pathways described herein, or augment or synergize the activity of any other compound or composition thereon.

The term "antagonist" as used herein refers to a compound or composition that can inhibit, suppress, block or negatively influence the intracellular signaling pathways described herein.

The term "sufficient amount" as used herein refers to a quantity of an agent that will result in the referred to effect.

The term "bind" as used herein refers to the interaction between ligands and their receptors, the binding being of a sufficient strength and for a sufficient time to allow the detection of said binding under the conditions of the assays disclosed herein.

The term "about" in reference to a numerical value means ±10% of the numerical value, more preferably ±5%, most preferably ±2%.

The term "administration" includes but is not limited to, oral, subbuccal, transdermal, parenteral, subcutaneous and topical. A common requirement for these routes of administration is efficient and easy delivery.

As used herein, the term "effective amount," refers to the amount required to achieve an intended purpose for both prophylaxis or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et at., Chapter 27 In: *Remington's Pharmaceutical Sciences*, 18th Ed., Gennaro, ed., Mack Publishing Co., Easton, Pa., 1990). Generally, the dosage required to provide an effective amount of a formulation, which can be adjusted by one skilled in the an, will vary depending on several factors, including the age, health, physical condition, weight, type and extent of the disease or disorder of the recipient, frequency of treatment, the nature of concurrent therapy, if required, and the nature and scope of the desired effect(s) (Nies et at., Chapter 3 In: *Goodman & Gilman's The Pharmacological Basis of Therapeutics*, 9th Ed., Hardman et al., eds., McGraw-Hll, New York, N.Y., 1996).

The term "nervous system cell" as used herein refers to all cells present in or derived from the nervous system, including, but not limited to neuronal cells, such as neurons, and non-neuronal cells, such as glial cells.

The term "transformed cell" as used herein refers to a cell that has been modified using procedures known in the art to express GFRα1 and/or not to express Ret.

The term "neuronal disease," as used herein, means any disturbance in structure or function of any nervous system cells, from whatever cause, and shall include all abnormalities, whether originating genetically or environmentally, present congenitally or later acquired, and from any cause, whether infectious, traumatic, toxic, degenerative, inflammatory or neoplastic. This shall include any neurodegenerative or retrogressive process within one or more cells of the nervous system, including even the death of nerves, axons, or tracts of the central nervous system.

The term "cellular response" as used herein refers to, without limitation, any change in neuronal survival, neuronal plasticity, neurite extension, cell migration, or any enhancement or inhibition of neurotransmitter synthesis and/or release.

The term "lipid rafts," as used herein, refers to a structure of sphingolipids and cholesterol packed into moving platforms within the liquid bilayer of cell membranes, and includes the detergent insoluble, glycolipid-enriched fraction that remains after extraction with Triton X-100 or similar detergents.

The terms "GPI-anchored" or "GPI-linked" as used herein in reference to a receptor refer to a receptor that is associated with GPI.

The term "independent intracellular signaling" in reference to a receptor as used herein refers to a receptor that evokes intracellular signaling without requiring and/or in the absence of co-receptors.

We surprisingly found that long-lasting $[Ca^{2+}]_i$ elevations were obtained in response to GDNF (10–100 ng/ml) in DRG neurons isolated from the Ret$^{-/-}$ mice. Investigation of this phenomena showed that GDNF-evoked $[Ca^{2+}]_i$ elevation persisted in nominally free extracellular $Ca^{2+}$ solution, and can be effectively blocked by either removing GPI-linked proteins, PLCγ inhibition or by the intracellular administration of low molecular weight heparin, an antagonist of IP$_3$-sensitive $Ca^{2+}$ release channels on internal stores. Thus in Ret$^{-/-}$ DRG neurons GDNF triggers the release of $Ca^{2+}$ from the internal $Ca^{2+}$ stores perhaps via the PLCγ-dependent $Ca^{2+}$ release pathway. Presently we cannot, however, exclude the existence of another calcium release mechanism. Unfortunately, U-73122 is not a selective inhibitor of only PLCγ and heparin may also have other effects that of a competitive block of the IP$_3$ binding sites at calcium release channels. Nevertheless, both low molecular weight heparin used in this study (Thorn et al., 1993; Meyer zu Heringdorf, 1998; Takei et al., 1998 and ref. thereafter) and U-73122 (Bourette et al., 1997; Davletov et al., 1998; Stam et al., 1998) are the most widely used pharmacological tools for complex investigation of PLCγ dependent signaling.

In the later phase of Ret-independent long-lasting $Ca^{2+}$ elevation, the calcium entry through calcium release activated channels (CRAC) would play a role in the maintenance of the elevated $[Ca^{2+}]_i$ due to balance refilling of intracellular $Ca^{2+}$ stores (Sharenberg and Kinet, 1998). Sustained elevations in $[Ca^{2+}]_i$ may lead to long term potentiation of various cellular responses, including, without limitation, major alterations in gene expression, neuronal plasticity, neurite extension, and neuron survivability, and may play an important role in such areas as learning ability, memory, epilepsy, and hearing loss, to name but a few. Potent capacitative calcium entry aimed in re-filling of depleted calcium stores exists in DRG neurons (Usachev et al., 1999).

We disclose that GDNF can stimulate a different pattern of $[Ca^{2+}]_i$ elevation in Ret-containing wild type and GFRα2$^{-/-}$ DRG neurons via the triggering of calcium release from heparin and PLCγ-sensitive internal stores. Ret tyrosine kinase has been shown to evoke a potent PLCγ activation through a PLCγ binding site (Borrello et al., 1996). Although there is a common view that in vivo GDNF preferentially binds to GFRα1 and NTN binds to GFRα2, GDNF at high concentrations in vitro can activate GFRα2 and NTN can bind to GFRα1 (Buj-Bello, 1997; Jing et al., 1997; Klein et al., 1997; Suvanto et al., 1997; reviewed by Airaksinen et al., 1999). To study the contribution of GFRα2 in the action of GDNF we investigated the effect of GDNF on $[Ca^{2+}]_i$ in GFRα2-negative (GFRα2$^{-/-}$) DRG neurons isolated from GFRα2 deficient mice (Rossi et at., 1999). We found that the GDNF-dependent $[Ca^{2+}]_i$ rise in DRG neurons was specifically dependent on GFRα1 activation, since GDNF evoked the same pattern of $[Ca^{2+}]_i$ elevation in GFRα2$^{-/-}$ neurons as in the wild type DRG neurons.

We also disclose that the Ret-independent GDNF-evoked intracellular signaling in neurons is much broader than activation of different patterns of $Ca^{2+}$ elevation. In addition to the GDNF evoked $Ca^{2+}$ rise we detected a potent GDNF-dependent transient activation of MAPK and CREB in Ret$^{-/-}$ DRG neurons. GPI-anchored protein-coupled kinases and Src-type kinases in particular, have been shown to evoke PLCγ stimulation, $[Ca^{2+}]_i$ elevation and MAPK activation (Brown and London, 1998; Dikic et al., 1996; Finkbeiner and Greenberg, 1998; Khare et al., 1997; Lutrell et al., 1996, 1997; Thomas and Brugge, 1997). Indeed in our experiments low doses of (4-amino-5-(4-methylphenyl)-7-(t-butyl)pyrazolo[3,4-d]pyrimidine (PP1) or (4-amino-5-(4-chlorophenyl)-7-(t-butyl)pyrazolo[3,4-d]pyrimidine (PP2) (both from Calbiochem), the potent and specific inhibitors of Src-type kinases, reversibly blocked GDNF-evoked $[Ca^{2+}]_i$ elevation in the Ret-negative DRG neurons as well as inhibited GDNF-dependent activation of MAPK in Ret-negative cell lines. Thus we wanted to investigate how GPI-anchored GFRα1 proteins lacking of an intracellular domain can, nevertheless, couple to and activate Src and MAP kinases at the cytoplasmic side of the membrane. To explore this question we used Ret-negative cell lines, SHEP neuroblastoma cells and NIH3T3 fibroblasts stably transfected with GFRα1 cDNA.

According to current understanding (Simons and Ikonen, 1997; Brown and London, 1998) GPI-anchored proteins, transmembrane tyrosine kinase proteins, G-proteins and acylated tyrosine kinases of the Src family all can associate with so-called lipid rafts, a structure of sphingolipids and cholesterol packed into moving platforms within the liquid bilayer (Sargiacomo et al., 1993, Simons and Ikonen, 1997; Brown and London, 1998; Luttrell et al., 1999; Viola et al., 1999). Whether or not such lipid rafts exist in DRG neurons is not known. It is also not known whether GDNF family receptors are included in the rafts. An association of Src type kinases with the inner leaflet of the raft by myristilation or palmyfilation links has already been demonstrated for many cell types, however (Brown and London, 1998).

To test whether GFRα1 can be coupled with a Src-type kinase within a raft, we performed experiments involving co-precipitation of kinases possibly coupled to the GFRα1 protein using GFRα1 antibodies in Triton X-100 detergent resistant membrane fractions. After Triton X-100 extraction, insoluble lipids and proteins remain in the form of detergent-insoluble glycolipid-enriched complexes(DIGs) or lipid rafts (reviewed by Simons and Ikonen, 1997). We disclose herein that Src-typo kinases can be co-precipitated with GFRα1 in DIGs from Ret$^{-/-}$ DRG neurons as well as in the different Ret-negative but GFRα1-expressing cell lines. In DIGs from SHEP neuroblastoma cells, GDNF evoked a potent transient activation of Src kinase. These findings indicate that activation of Src-type kinases by GDNF in Ret-negative DRG neurons and neuroblastoma cells might occur within the lipid rafts.

As in the wild type DRG neurons, GDNF evoked potent activation of p42/p44 MAPK and CREB in the different Ret-deficient cell lines. Again GDNF-evoked phosphorylation of MAPK was completely abolished with low doses of the selective Src kinase inhibitor, PP2. By immunostaining with anti-phosphorylated MAPK antibodies we also found that phosphorylated MAPK is effectively translocated to the nucleus of SHEP cells and this translocation was modulated by PP2 (Poteriaev and Titievsky, unpublished observations). Thus GDNF-evoked Ret-independent phosphorylation of MAPK is completely dependent on the GDNF-evoked activation of a Src type kinase. Since the studies on neuronal survival showed that MAPK effectively phosphorylates CREB, it was of great interest to reveal the downstream targets of activated MAPK in Ret-negative neurons and cell lines. Indeed, we detected significant GDNF-dependent activation of CREB both in the Ret$^{-/-}$ DRG neurons and the SHIP cells. Our results are therefore to some extent contradictory to those of Trupp et al. (1999), which found that GDNF Ret-independently activates CREB phosphorylation but not Ras/ERK pathway in RN33B cells. In addition to the detection of potent GDNF-dependent ERK1/ERK2 activation, we observed a significantly prolonged kinetic of CREB activation in SHEP cells as compare to the Trupp et al. (1999) study conducted in RN33B cells. Interestingly, we also observe a robust GDNF-dependent activation of the CREB-related protein ATF-1 in Ret-negative SHEP cells but not in the Ret$^{-/-}$ DRG neurons. It is, therefore, possible that the noticed discrepancies between our results and those reported by Trupp et al. (1999) reflect the variance between the different type of the cells.

Src kinases and MAPK might significantly affect cell function since these kinases have been established to be crucially involved in mitogenesis, nerve-growth factor induced cell differentiation with neurite outgrowth, cell migration as well as in focal adhesion kinase (FAK) dependent cell motility (Khare et al., 1997; Thomas and Brugge, 1997). A potent MAPK activation, such as observed in our experiments, might promote neuronal survival and neuronal plasticity (reviewed by Fukunaga K. & Miyamoto E., 1998 and Impey et al., 1999). At the moment, however, we do not know the exact physiological meaning of the GDNF invoked long-lasting $Ca^{2+}$ elevation and MAPK and CREB activation in Ret$^{-/-}$ DRG neurons and in the cell lines. Ret-independent GDNF-evoked activation of the transcription factors of the CREB family can lead to a potent up-regulation of the gene's expression. This can result in the profound changes in neuronal plasticity (Finkbeiner et al., 1997), since it has been shown that MAPK signaling facilitates memory consolidation and long-term potentiation by promoting de novo CREB-regulated gene expression (reviewed by Impey et al., 1999). Unfortunately, the study of the possible changes in neuronal plasticity invoked by GDNF in Ret$^{-/-}$ or GFRα1 deficient neurons is precluded by the early postnatal death of the knock-out animals. It would appear that DRG neurons do not use this GFRα1-mediated signaling as a survival factor, as GDNF has also not been shown to stimulate survival of Ret$^{-/-}$ DRG neurons in culture (unpublished observations and Taraviras et al., 1999). We recently showed, however, that GDNF promotes survival of postnatal cochlear sensory neurons, which express GFRα1 mRNA but lack Ret mRNA (Ylikoski et al., 1998). The morphological;and biological consequences which might be triggered by GDNF-evoked Ret-independent signaling remain to be elucidated, but it is clear that different neuronal populations use this signaling pathway for different purposes and with different results.

One question that remains is how a signal is passed from the outer leaflet of the raft to the inner one, or how it is passed from the outside part of the membrane to the inner one? Without intending to be limited by any theory or mechanism, we propose that there may be an unknown transmembrane protein linking GFRα1 and Src-type protein kinase that serves as the transducer of the signal. One such adapter plasma membrane-associated protein has been found recently in DRG neurons (Lang et al., 1998). In our experiments an about 72 kD unrecognised protein was immunoprecipitated with GFRα1 antibodies. However, the interaction of a potential adapter protein with GFRα1 should be different from the Ret-GFRα1 coupling. The soluble GFRα1, capable of inducting MAPK phosphorylation in the presence of GDNF in Ret-expressed cells, was unable to evoke intracellular signaling in the Ret-negative parental NIH3T3 fibroblasts. Based on these experiments we conclude that if an adapter protein exists, it would, unlike Ret, strictly require an association with the GPI anchor of GFRα1. Another possibility may be that enzymes activated in the rafts involved in anchor release might yield soluble phospho-oligosaccharides. These would then flip across the bilayer and may function as active second messengers in the cytosol. GDNF can also trigger lipid-lipid interaction and raft coalescence-dependent accumulation of intracellular phosphorylated proteins. Whether such signaling pathways are involved in the action of GDNF is presently unknown.

In summary, we have found that GDNF evokes $[Ca^{2+}]_i$ elevation and Ret-independent activation of Src-tyrosine kinase, PLCγ, MAPK and CREB—coupled intracellular signaling pathways in Ret$^{-/-}$ DRG neurons and in the Ret-negative cell lines GDNF binds to the GPI-anchored GFRα1 with subsequent activation of Src kinases associated with GFRα1 followed by activation of MAPK, CREB, PLCγ and sustained elevation of $[Ca^{2+}]_i$. The proposed signaling pathway is summarized in FIG. 9.

EXAMPLES

Materials and Methods

Neuronal Cultures

DRG from embryonic day 18 (E18) mice were treated with trypsin (Worthington), non-neuronal cells removed by preplating, and about 95% pure neurons cultured on poly-ornithine-laminin-coated glass coverslips in Ham's F14 medium (Imperial Laboratories) with serum substitute containing NGF, BDNF and NT-3 (all from PeproTech, 2 ng/ml if each) for at least 1 day before measurement. Neurotrophins were extensively washed out before GDNF application. GDNF was from PeproTech and donated by Cephalon, Inc. Ret-deficient mice (Schuchardt et al., 1994) were identified from heterozygote matings by the absence of kidneys and PCR-based genotyping. GFRα2-deficient mice were obtained from homozygote matings (Rossi et al., 1999).
$[Ca^{2+}]_i$ Measurement $[Ca^{2+}]_i$ was measured using a Bio-Rad MRC-1024 confocal microscope equipped with an argon-krypton laser. The cells were loaded with 10 μM Calcium Green-1AM (Molecular Probes), a membrane permeable $Ca^{2+}$ dye, by 30 min incubation in serum free cell-culture media at 37° C. and 5% $CO_2$. After loading, the neurons were kept at room temperature in Dulbecco's PBS solution contained 20 mM HEPES (pH=7.4) for at least 20 min prior to the experiments. All compounds were applied to the bath by a peristaltic pump. 6 kD Heparin (Sigma) and Alexa 568 nm fluorescent dye (Molecular Probes) were loaded into the cells using Molecular Probes' pinocytotic influx loading reagent basically according to the manufacturer instructions. The loading did not affect neuronal viability throughout the experiments. Cell injection was performed using Eppendorf microinjection system. The average intensity of fluorescence in the predefined ROI (Region Of Interest) was measured on-line using TimeCourse software from BioRad. The calibration of fluorescence traces was performed in vitro using $F_{max}$ and $F_{min}$ values obtained with the calcium calibration buffer kit (Molecular Probes). Because the calibration solutions may not reflect the intracellular environment, the experimental data are presented as delta $[Ca^{2+}]_i$ calculated using $K_d$=190 nM for Calcium Green-1.
Transgenic GFRα2 Mice Transgenic GFRα2 knock-out mice were produced in our laboratory. To isolate GFRα2 genomic clones, we screened a mouse 129/Sv library (Stratagene) with a rat GRFα2 cDNA fragment as a probe. A 6.7 kb HindIII-XBAI fragment was used to construct the targeting vector. A 0.5 kb NotI-XbaI fragment of the GFRα2 gene, containing part of the first coding exon with the translation initiation site, was replaced with a 2.0 kb cassette containing the neomycin-resistance gene (neo) driven by the PGK promoter and polyadenylation signal. R1 embryonic stem cells were electroporated with linearized plasmid and selected in G418 (250 ug/ml). Resistant clones were screened by Southern blot analysis using a 5' outside probe that recognizes a 7.8 kb wild-type and 5.5 kb mutant band after a BamHI digest. Positive clones were further hybridized with neo and 3' outside probes to exclude random integration of the vector. Two injected clones gave germline transmission, when the chimeras were crossed to C57BL/6JO1aHsd.
Single Cell RT-PCR A negative pressure was applied to the micropipette, and the whole cell was harvested under visual control. The content of the pipette was expelled into a test tube containing Trizol™ reagent lysis buffer (Gibco BRL) and 1 μg of carrier tRNA. The total RNA was isolated and the RT-PCR reaction was performed using a Titan™ One Tube RT-PCR kit (Boehringer Mannheim) according to the manufacturer's instructions. One half of the material from each neuron was used to amplify GFRα1 mRNA. The presence of total RNA in a sample was ensured by the amplification of a 216 bp fragment of cyclophilin mRNA using the second half of the material. For cyclophilin amplification, the primers from a QuantumRNA™ kit (Ambion, Tex.) were used. The primers used for analysis of GFRα1 expression were as follows: 5'-GCGGCACCATGTTCCTAGCC-3' (SEQ ID NO: 1) and 5'-CAGACTCAGGCAGTTGGGCC-3' (SEQ ID NO: 2). The primers were designed to cross at least one intron and to exclude amplification from genomic DNA. Amplification was carried out for 45 cycles at 95° C. for 45 s; 62° C. for 45 s; and 72° C. for 60 s. The resulting fragments were identified by Southern blotting with a $^{32}$P-labelled cDNA insert of the mouse GFRα1 clone and a cDNA fragment of cyclophilin. Radioactive signals were detected with a Fuji Bioimage analyzer BAS 2000. No fragments were obtained from the media of cultured neurons.
RT-PCR Analysis of GDNF Receptors in Cultured DRG Neurons and SHEP Neuroblastoma Cell Line Total RNA from cultured DRG neurons (approximately 200 cells) was divided into three equal parts and the RT-PCR was carried out as above. The primers for GFRα2 were: 5'-TATTGGAGCATCCATCTGGG-3' (SEQ ID NO: 3) and 5'-AGCAGTTGGGCTTCTCCTTG-3' (SEQ ID NO: 4), and for Ret they were: 5'-ATGAAAGGGTACTGACCATGG-3' (SEQ ID NO: 5) and 5'-AGGACCACACATCACITTGAG-3' (SEQ ID NO: 6). The PCR was carried out for 40 cycles under the conditions indicated above. In the RT-PCR analysis of SHEP cells we used the primers for human GFRα1, GFRα2 and Ret. The primers sequences and PCR conditions were reported by Hishiki et al. (1998).

Immuno-complex Kinase Assays and Immunoblotting

DRG neurons ($5\times10^5$), SHEP neuroblastoma cells ($10^7$), Neuro2A neuroblastoma cells stably transfected with GFRα1 ($10^7$) or NIH3T3 cells (NIH3T3/pBpGFRα1) stably transfected with GFRα1 ($10^7$) were incubated in serum-free culture medium without (control) or with GDNF (GDNF-treated) for 0.5–15 min at 37° C. The cells were washed twice with cold PBS/vanadate and lysed in TX-100 lysis buffer (50 mM Tris-HCl, pH 7.5, 150 mM NaCl, 5 mM EDTA, 1% Triton X-100, 1 mM sodium orthovanadate, 1 mM phenylmethylsulfonyl fluoride (PMSF) and protease inhibitors (Boehringer) on ice for 1 hour. The postnuclear lysates were pre-cleared by incubation with 50 μl of 50% Protein G-Sepharose for goat polyclonal antibodies or Protein A-Sepharose CL4B (Pharmacia) for rabbit polyclonal antibodies for 1 hour at +4° C. After removal of the beads, the supernatants were incubated with 0.4–0.5 μg of anti-GFRα1 or anti-Yes polyclonal antibodies (Santa Cruz Biotechnology) overnight at +4° C. followed by incubation with Protein G or A-Sepharose for 2 hours. The immuno-complexes were washed twice in TX-100 lysis buffer without EDTA and twice in kinase buffer (25 mM Hepes, pH 7.4, 5 mM $MgCl_2$, 5 mM $MnCl_2$, 1 mM sodium orthovanadate). Immunocomplexes were incubated in a kinase buffer supplemented with 5–10 μCi of [$\gamma$-$^{32}$P]ATP for 20 minutes at 37° C. The samples were washed out from incorporated label and were subjected to 10% SDS-PAGE. Proteins were transferred to a Hybond ECL membrane (Amersham) using semi-dry blot apparatus (Schleicher & Schuell, Dassel, FRG). Labeled proteins were visualized with a Fuji Bioimage analyzer BAS 2000 or by autoradiography. Quantification of the optical density of the blots was performed using the TINA program.

For immunoblotting, the membranes were probed with Src-2 antibodies (Santa Cruz Biotechnology) recognizing c-Src, Fyn and Yes, followed by the secondary HRP-conjugated anti-rabbit antibodies (Sigma). The membranes were developed with ECL reagents (Amersham Life Science).

Immunoprecipitation and Western Blotting of PLCγ

To determine changes in GDNF-evoked PLCγ tyrosine phosphorylation the Western blotting assays were performed as described in Khare et al. (1997). Briefly, SHEP neuroblastoma cells were pre-incubated with 1 mM sodium vanadate in serum-free medium for 30 min. at 37 ° C. and then were treated at 37 ° C. with 1–100 ng/ml GDNF for 1 min. unless otherwise indicated. Incubation was stopped by the addition of ice-cold PBS buffer containing 1 mM sodium vanadate. Whole cell lysates (final protein concentration 0.1–0.3 mg/ml) were prepared at 4° C. in an extraction buffer (pH 7.5) containing 50 mM Tris-HCl, 137 mM NaCl, 1 mM sodium vanadate, 1 mM PMSF, 10% glycerol, 1% NP-40 and protease inhibitors cocktail (Boehringer). Phosphotyrosine-containing proteins were immunoprecipitated with 4G-10 antibodies (Upstate Biotechnology), collected with Protein A Sepharose beads and separated on the 7.5% SDS-PAGE. The proteins were transferred to Hybond-ECL nitrocellulose membrane, and PLCγ was assessed by Western blotting using anti-PLCγ antibodies (Upstate Biotechnology). In some experiments we first immunoprecipitated PLCγ from the cell lysate using anti-PLCγ antibodies and probed the filter with anti-phosphotyrosine 4G-10 antibodies as described above. In these experiments after the phosphotyrosine detection of the immunoprecipitates, the membranes were stripped and re-probed with anti-PLCγ antibodies (Upstate Biotechnology). Membranes were developed with ECL reagents.

MAPK, JNK and CREB Phosphorylation Assays

To assess GDNF-dependent MAPK and CREB phosphorylation in all studied cell lines, the semiconfluent cell monolayers were starved for 3 hours in serum-free medium, and then GDNF was applied for the indicated time. For the analysis of MAPK and CREB activation in Ret$^{-/-}$ animals the DRG neurons were dissected from E18 mice and maintained in NGF-containing medium for 2 hours. After this time the neurons were deprived of NGF by placing them in NGF-free medium in the presence of anti-NGF antibodies. After 2 hr without NGF, the neurons were stimulated with GDNF. In the experiments involving Src-kinase inhibition, a Src-family kinase inhibitor PP2 was added at the indicated concentrations to the cell monolayers 5 min before GDNF application. In some experiments 1 μg/ml of soluble GFRα1 lacking a GPI anchor (GFRα1/Fc chimeric protein; R&D systems) was added 5 min prior to the GDNF application and was kept in the solution during the GDNF treatment, After stimulation, the cells were briefly washed with PBS/sodium vanadate and lysed in the buffer containing TBS, 2 mM EDTA, 1% NP-40, 1% Triton X-100, 1 mM PMSF, 1 mM $Na_3VO_4$ and a Complete, protease inhibitors cocktail (Boehringer Mannheim). Total cell protein for each extract was measured by MicroBSA (Pierce) and an equivalent amount of protein was resolved electrophoretically on 10% polyacrylamide gels. The proteins were transferred to a Hybond ECL (Amersham) membrane and the blot was probed with either MAPK (ERK1/2) or JNK Anti-Active™ pAbs (Promega) according to the manufactrer's instructions. The blots were then reprobed with GFRα1 mAbs (Transduction Laboratories). In the CREB phosphorylation study, Western blots were probed with the antibodies that specifically recognise the Ser-133 phosphorylated form of CREB and then re-probed with the anti-CREB antibodies New England Biolabs).

Example 1

Figure 1F:
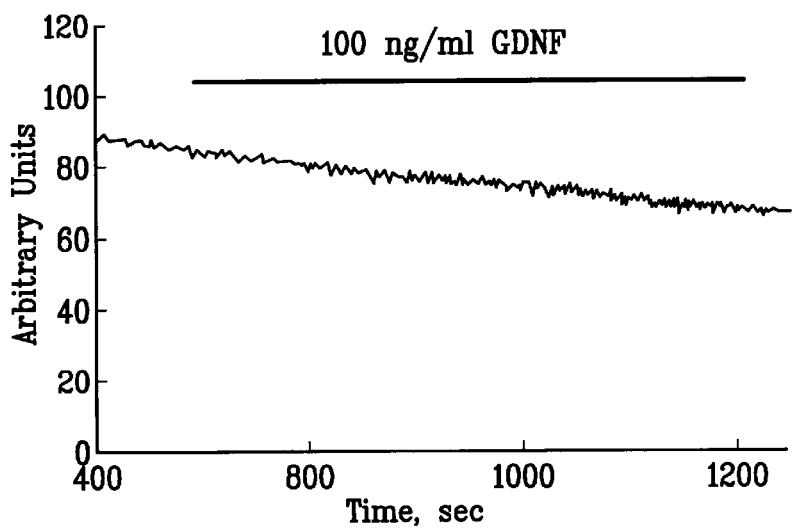
Figure 1E:
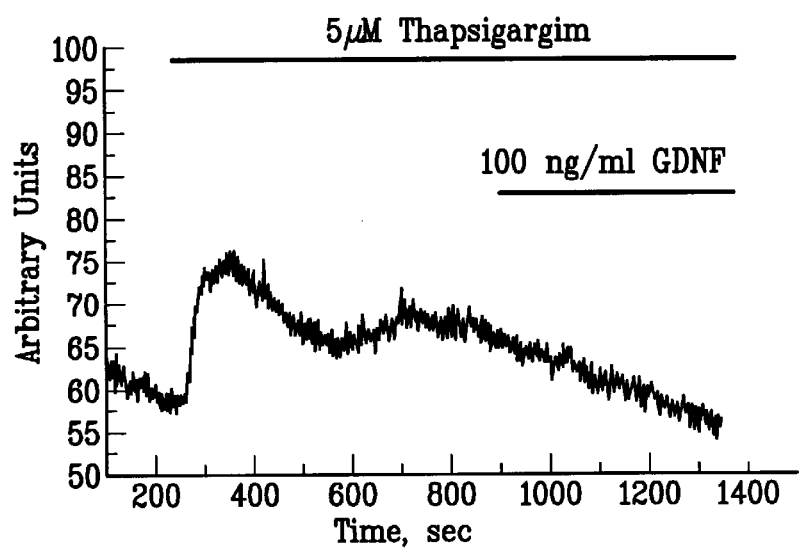

Effect of GDNF on $[Ca^{2+}]_i$ in Ret/GFRα1 Positive Wild Type and GFRα2$^{-/-}$ DRG Neurons In order to investigate a possible Ret-independent GDNF signaling in neurons we followed GDNF-induced changes in intracellular $Ca^{2+}$ concentration ($[Ca^{2+}]_i$) by confocal microscopy in Ret-expressing and Ret$^{-/-}$ DRG neurons. Two different types of GDNF-evoked changes in $[Ca^{2+}]_i$ were observed in 60–70% of the wild type DRG neurons expressing both Ret, GFRα1 and GFRα2 (FIG. 1C). GDNF (10 ng/ml) induced a rapid transient increase in $[Ca^{2+}]_i$ whereas the concentrations over 10 ng/ml (10–100 ng/ml) evoked both a transient and slow long-lasting elevation in $[Ca^{2+}]_i$ (FIG. 1A) (n=15 experiments; at least 3–4 neurons were recorded in each experiment). To control the specificity of the observed GDNF-evoked long-lasting $Ca^{2+}$ elevation, we used heat-inactivated GDNF. Heat-inactivated GDNF did not evoke any changes of basal $[Ca^{2+}]_i$ (8 recorded cells). (FIG. 1B). To monitor the functionality of the internal calcium pools at the end of the experiments we usually applied 5 μM thapsigargin, an inhibitor of SERCA pump at intracellular calcium stores. All cells responded to the application of thapsigargin with a profound elevation in $[Ca^{2+}]_i$ (two representative recordings shown on FIG. 1B). Further control experiments were performed using cleavage of GPI-anchored proteins from the membrane with phosphatidylinositol-specific phospholipase C (PI-PLC) (7 recordings). None of the pre-treated neurons responded to the application of GDNF (100 ng/ml) (FIG. 1D). Depletion of intracellular $Ca^{2+}$ stores with 5 μM thapsigargin (5 recordings) or pre-treatment of neurons with the PLCγ inhibitor, U-73122 (6 recordings) also resulted in the abolishing of the effect of GDNF (FIGS. 1E and 1F respectively). Consistent with the specificity of GDNF (Rossi et al., 1999) responded to GDNF with the same pattern of fast and slow kinetics of $Ca^{2+}$ elevation as the wild type neurons (FIG. 1G) (9 recordings). Nominal removal of extracellular calcium (with no added EDTA to the extracellular media $[Ca^{2+}]_o$ was about 20 μM) led to decline in $[Ca^{2+}]_i$. Interestingly, application of GDNF in these cells resulted in a profound rapid and oscillatory (5 out of 9 cells) $[Ca^{2+}]_i$ increase (FIG. 1D). Switching the perfusion back to the calcium-containing medium resulted in a profound calcium overshoot. Our results are consistent with a recent report, showing that depletion of intracellular calcium stores in DRG neurons evoke a substantial calcium entry aiming to re-fill these stores (Usachev et al., 1999).

Example 2

Effect of GDNF on $[Ca^{2+}]_i$ in $Ret^{-/-}$, GFRα1 Positive DRG Neurons

Figure 2A:
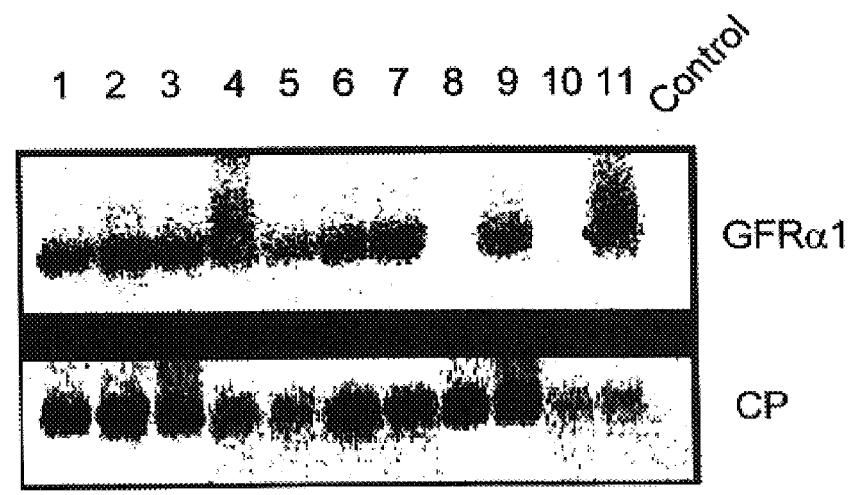
FIGS. 2 A–D depict GDNF-triggered $Ca^{2+}$ release from the heparin-sensitive internal calcium stores in Ret (Ret-negative) DRG neurons. A. Single cell RT-PCR was performed in 18 Ret$^{-/-}$ DRG neurons. Upper panel shows GFRα1 mRNA expression pattern in 11 cells. Cyclophilin (CP, lower panel) was used as a control. 16 out of 18 studied neurons expressed GFRα1 mRNA. B. GDNF (100 ng/ml)-evoked long-lasting $Ca^{2+}$ elevation in Ret$^{-/-}$ DRG neurons (the two traces are representative of 41 recordings. The vertical bars depict d$[Ca^{2+}]_i$ changes of 100 nM. C. Pre-treatment with PI-PLC (1 U/ml; for 1 hr at 37° C.) abolished the effect of GDNF because of removal of the GPI-anchored proteins from the membrane. To control the viability of the cells at the end of experiments the neurons were treated with thapsigargin (5 μM) and were also depolarized with 50 mM K+. After thapsigargin or K+ treatment $[Ca^{2+}]_i$ was transiently increased indicating that the internal $Ca^{2+}$ stores and voltage-operated $Ca^{2+}$ channels were functional. The vertical bars depict $d[Ca^{2+}]_i$ changes of 100 nM. D. In two separate experiments, part of the neurons pre-loaded with Ca-green were injected with heparin. Control neurons were injected with the solvent. Heparin injected neurons (indicated with #2, lower trace, n=3 neurons) did not significantly respond to GDNF application whereas control neurons responded with a long-lasting $[Ca^{2+}]_i$ elevation which was slowly declining during wash-out (indicated with #1, upper trace, n=3 neurons). Vertical bar depicts $d[Ca^{2+}]_i$ changes of 100 nm.
Figure 2B:
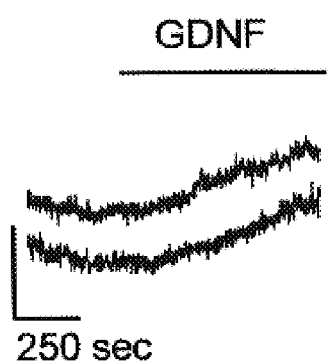
Figure 2C:
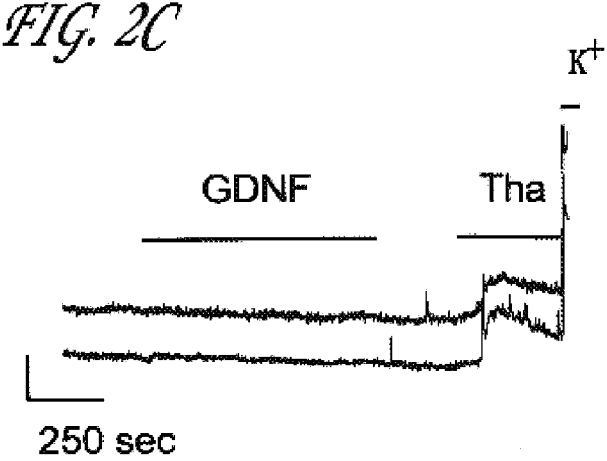

Ret tyrosine kinase can activate cytoplasmic PLCγ through the PLCγ docking site (Borrello et al., 1996), and this could lead to $IP_3$ production and subsequent $Ca^{2+}$ release. We therefore assessed the role of Ret in the GDNF-evoked calcium signaling using DRG neurons, isolated from $Ret^{-/-}$ mice (Schuchardt et al., 1994). In 16 out of 18 tested $Ret^{-/-}$ DRG neurons we detected GFRα1 mRNA (11 representative lanes shown on FIG. 2A) meaning, in agreement with a recently published observation (Natarjan et al., 1999), that $Ret^{-/-}$ neurons preserved the expression of GFRα1 mRNA well. Surprisingly, although we never observed a GDNF-dependent fast $[Ca^{2+}]_i$ rise in these neurons, a long-lasting $[Ca^{2+}]_i$ elevation was recorded in response to 10–100 ng/ml GDNF in 60–70% of the neurons (FIG. 2B) (n=21 experiments, 41 out of 61 neurons responded). In the control experiments DRG neurons did not respond with $[Ca^{2+}]_i$ elevations to changes of the superfusion solutions, brief switch on/off of the peristaltic pump, or prolonged application of heat-inactivated GDNF (100 ng/ml) (3 experiments, data not shown; the experimental conditions were identical to experiments with wild type DRG neurons, see FIG. 1B). In addition the prolonged application of GDNF did not affect $[Ca^{2+}]_i$ in $Ret^{-/-}$ neurons pre-treated with PI-PLC (FIG. 2C, 3 recordings). As in the experiments with wild type DRG neurons, the viability of the neurons was verified either by depletion of intracellular stores with thapsigargin (5 μM) or by neuronal depolarization evoked by 50 mM external $K^+$ (FIG. 2C).

Example 3

Figure 2D:
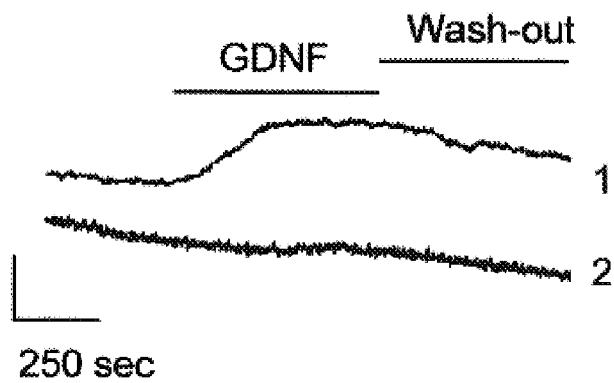

GDNF Triggers $Ca^{2+}$ Release from the Internal Stores in Ret Negative DRG Neurons Activation of PLCγ apparently leads to $IP_3$ production and subsequent $Ca^{2+}$ release from $IP_3$ sensitive stores. To block $IP_3$ receptors on internal $Ca^{2+}$ stores, we either injected DRG neurons with an intracellular-like solution containing 6kD heparin, a competitive antagonist of the $IP_3$ binding sites at the $IP_3$-sensitive $Ca^{2+}$ release channels (Berridge, 1998) or loaded heparin into the cells using a pinocytotic loading reagent in a mixture with Alexa 568 fluorescent dye (n=2 experiments). In the heparin injected neurons, GDNF did not evoke an increase in $[Ca^{2+}]_i$ in comparison to the saline injected control neurons (FIG. 2D). Neurons loaded by pinocytosis with heparin and the Alexa dye replied with $[Ca^{2+}]_i$ elevation in response to both thapsigargin and to high extracellular $K^+$-evoked depolarization. They, however, did not respond either to 100 nM GDNF or to 10 μM ATP (data not shown). The GDNF-evoked long-lasting $[Ca^{2+}]_i$ elevation was completely abolished by pre-treatment of Ret, neurons with U-73122, an inhibitor of PLCγ (n=3 experiments, data not shown). Taken together, these results indicate that in Ret-negative DRG neurons GDNF can trigger $Ca^{2+}$ release from $IP_3$-sensitive internal calcium stores via the GFRα1/PLCγ coupled pathway.

Example 4

Effect of GDNF on Calcium Entry

Figure 3A:
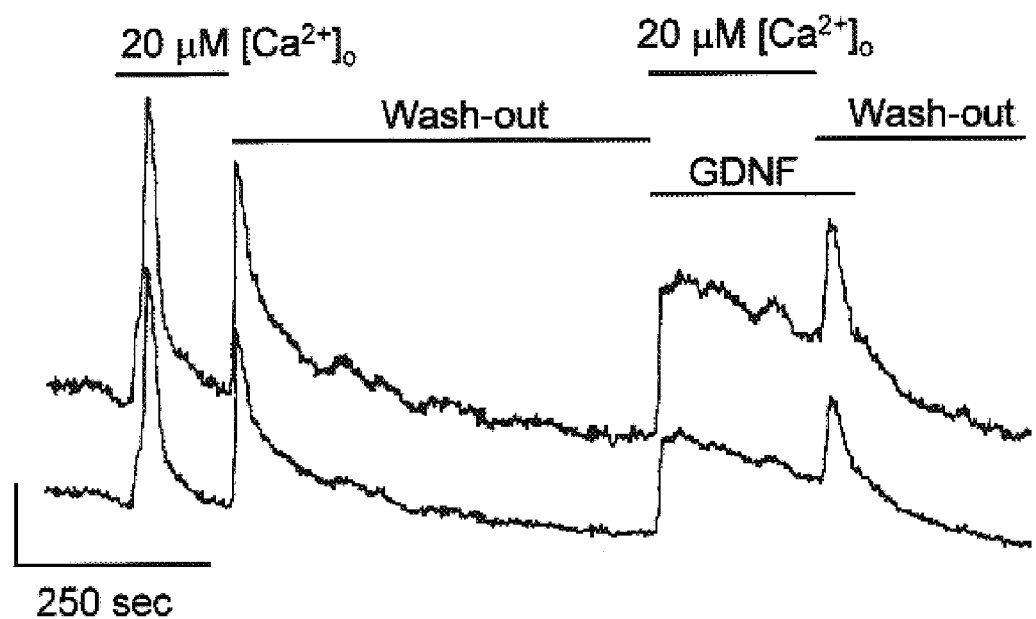
FIGS. 3 A–E A. In part of the DRG neurons, application of nominally $Ca^{2+}$ free extracellular solution (no added EGTA) resulted in a delayed transient $[Ca^{2+}]_i$ elevation possibly due to activation of capacitative calcium entry (15 recorded neurons). This $[Ca^{2+}]_i$ overshoot was not observed when calcium concentration in the nominally $Ca^{2+}$ free external solution was clamped to about 1 nM with 2 mM EGTA (14 recorded neurons; data not shown). A return to 2 mM external $Ca^{2+}$ (wash-out) resulted in a pronounced $[Ca^{2+}]_i$ overshoot indicating an increased membrane permeability for $Ca^{2+}$. Switching back to nominally $Ca^{2+}$ free external media in the presence of GDNF (100 ng/ml) resulted in a transient elevation of $[Ca^{2+}]_i$ with significantly prolonged kinetics of $[Ca^{2+}]_i$ decline. This indicates that at the resting membrane potential GDNF can prolong capacitative calcium entry either via more profound depletion of the internal stores or by a direct action on calcium channels in the plasma membrane. The traces are representative of 14 recordings performed in 3 independent experiments. B. GDNF was repeatedly applied both in the presence of the normal extracellular $Ca^{2+}$ concentration and in the presence of nominally $Ca^{2+}$ free external solution in $Ret^{-/-}$ DRG neurons. Application of GDNF (100 ng/ml) in the normal calcium extracellular solution evoked a typical long-lasting $Ca^{2+}$ elevation which was reversed by wash-out A switch to the nominally $Ca^{2+}$ free external solution in the continues presence of GDNF resulted in profound (and oscillatory in 5 out of 12 recordings) increase in $[Ca^{2+}]_i$ followed by slow decline in $[Ca^{2+}]_i$. Removal of GDNF (marked with arrow 1) led to a significant decline in $[Ca^{2+}]_i$. Readmission of GDNF led to quick elevation in $[Ca^{2+}]_i$ (arrows 2 and 3) (12 recorded neurons). Switching back to normal external $Ca^{2+}$ containing solution resulted in an additional capacitative overshoot in $[Ca^{2+}]_i$. C. Pre-treatment with 10 μM U-73122 inhibited release of $Ca^{2+}$ from the internal stores of Ret-negative DRG neurons and also in Ret-positive, but GFRα2-negative DRG neurons. D. The GDNF-evoked GPI linked protein-dependent sustained $[Ca^{2+}]_i$ elevation in Ret-negative DRG neurons was abolished by pre-treatment with 1 U/ml PI-PLC. E. Shows effect of pre-treatment with 5 μM thapsigargin on GDNF-evoked $[Ca^{2+}]_i$ changes in wild type DRG neurons.
Figure 3B:
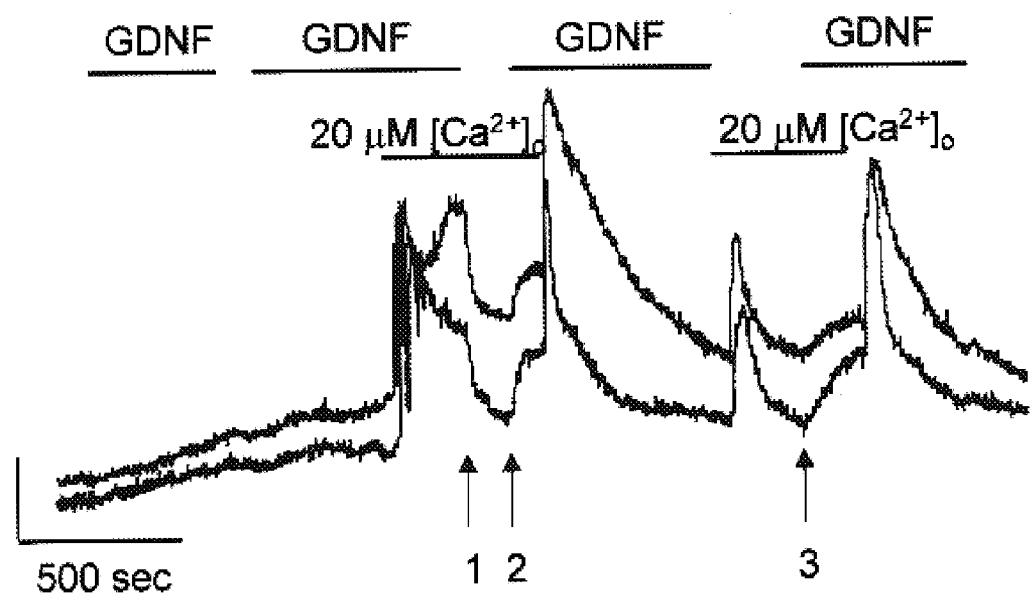
Figure 3C:
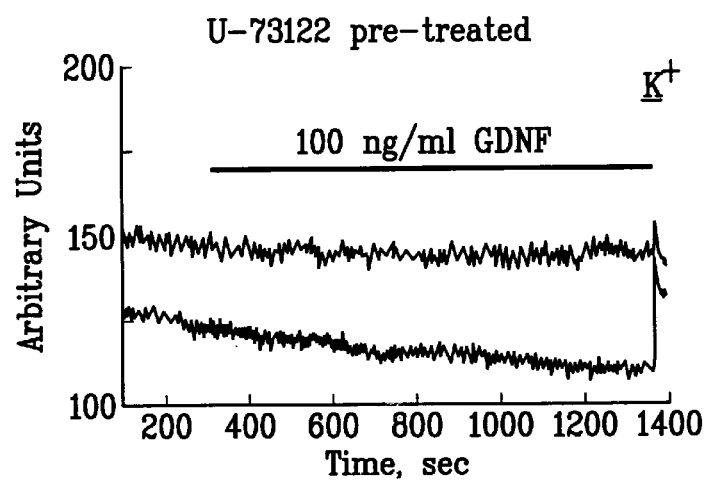
Figure 3D:
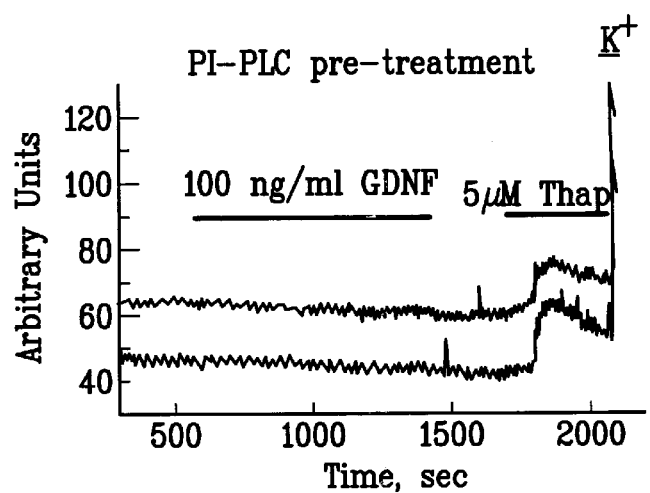
Figure 3E:
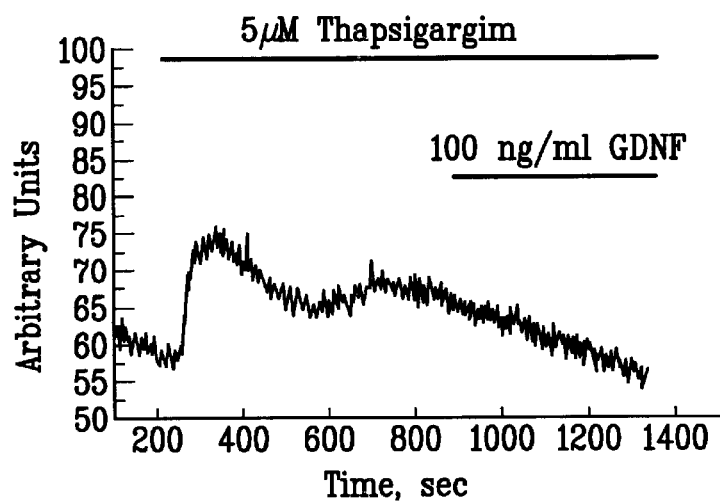

We hypothesized that in addition to the GDNF-evoked release of sequestered $Ca^{2+}$, entry of extracellular $Ca^{2+}$ would participate in the maintenance of the elevated $Ca^{2+}$ level observed after stimulation with GDNF. Furthermore, it has recently been shown that depletion of intracellular calcium stores in DRG neurons results in a substantial capacitative calcium entry (Usachev et al., 1999). In 15 out of 24 $Ret^{-/-}$ neurons the switch to nominally $Ca^{2+}$ free external solution ($[Ca^{2+}]_o$ about 20 μM $Ca^{2+}$; the gradient of calcium over the plasma membrane was still about 200-fold under these conditions) resulted in pronounced $Ca^{2+}$ overshoot (FIG. 3A). Since this overshoot was never observed in the cells bathed in an external solution containing 2 mM EGTA ($[Ca^{2+}]_o$ about 1 nM; n=14 recordings, data not shown) we suggest that the perfusion of some cells with nominally calcium free solution resulted in a rapid depletion of very labile calcium pools and concomitant capacitative entry of calcium. The refilling of intracellular stores at 20 μM external calcium was not complete, since re-addition of normal (2 mM calcium containing) extracellular solution resulted in an additional large calcium overshoot Re-application of GDNF in the presence of low extracellular calcium (FIG. 3A) (traces are representative of 15 recordings) evoked a massive $[Ca^{2+}]_i$ overshoot and substantially slower decay kinetics, compared with control application of nominally calcium free extracellular solution only (FIG. 3A). We concluded that GDNF prolonged capacitative calcium entry either via additional depletion of intracellular stores or via a direct effect on the plasma membrane calcium release activated channels (CRAC). In another set of experiments we tested if the prolonged decay of calcium entry is dependent on the direct action of GDNF on CRAC. In these experiments we removed GDNF from the nominally calcium free extracellular media at the middle of calcium overshoot. Representative traces of 12 recordings performed in $Ret^{-/-}$ DRG neurons in three separate experiments are shown on FIG. 3B. Application of GDNF (100 ng/ml) in normal calcium-contained extracellular solution resulted in the usual long-lasting $[Ca^{2+}]_i$ elevation interrupted with a wash-out period. Switching to nominally calcium free (about 20 μM free calcium-containing) extracellular solution resulted in a large calcium overshoot, similar to that shown in FIG. 3A. During the $[Ca^{2+}]_i$ decay GDNF was removed from the external media (indicated on FIG. 3B with arrow 1). This resulted in rapid decline of $[Ca^{2+}]_i$ suggesting that GDNF may have a direct regulatory effect on the plasma membrane CRAC, rather than an indirect effect mediated via depletion of calcium from internal stores. Re-addition of GDNF (100 ng/ml; indicated with arrows 2 and 3) in the nominally free calcium solution resulted in a profound increase in $[Ca^{2+}]_i$ (FIG. 3B; 12 recorded neurons).

Example 5

Figure 9A:
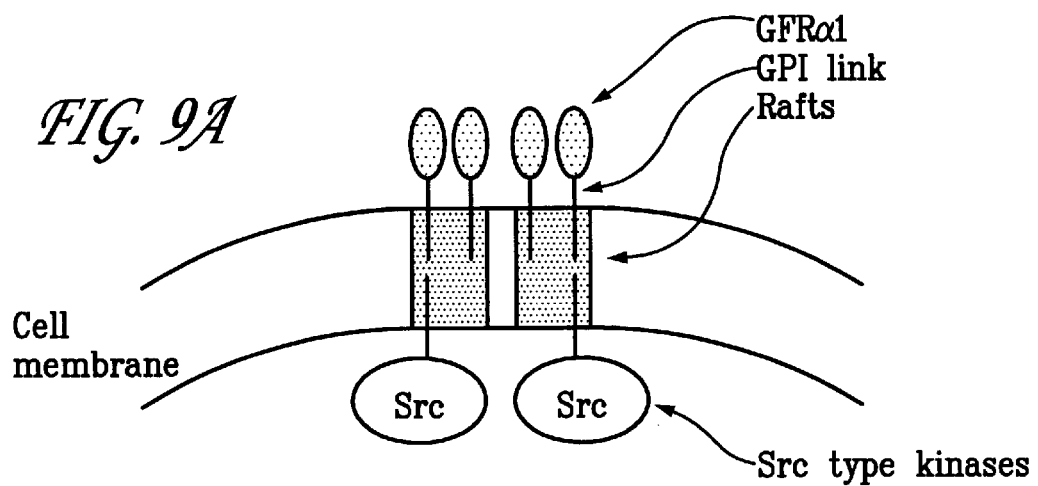
FIGS. 9 A–C depict a schematic representation of the proposed Ret-independent GDNF-evoked signaling pathway. The GDNF-triggered membrane signaling most probably occurs within lipid rafts, as GFRα1 protein can be co-precipitated with Src type kinases in Triton X-100 insoluble membrane fractions. GDNF-evoked activation of GFRα1 induces Src type kinase (in particular, pp62$^{Yea}$ kinase in SHEP cells) activation and subsequent phosphorylation of PLCγ and MAP kinases. PLCγ activation leads to $IP_3$-dependent release of $Ca^{2+}$ from internal calcium stores. Src-dependent phosphorylation of MAPK lead to its translocation to the nucleus and CREB activation.
Figure 9B:
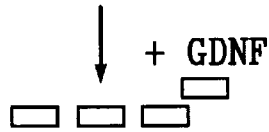
Figure 9C:
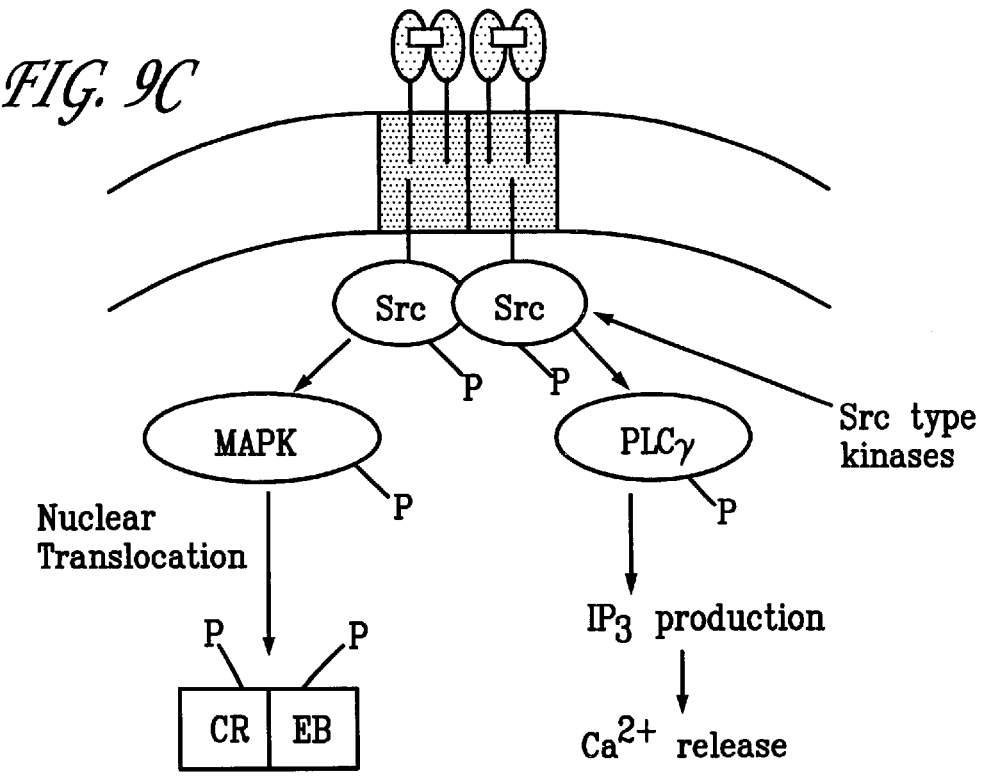

GDNF Activates a GFRα1-Coupled Kinase, MAP Kinases and cAMP Response Element Binding Protein (CREB) in $Ret^{-/-}$ DRG Neurons Since the effect of GDNF on $[Ca^{2+}]_i$ in Ret-deficient DRG neurons is specifically dependent on the presence of a GPI-anchored receptor, we focused on a signaling pathway linked to Ret-independent GDNF-evoked activation of GFRα1. GPI-anchored proteins have been shown to be localized to lipid rafts and directly associated with Src family kinases (Berridge, 1998; Harder et al., 1998). There is much evidence suggesting that Src family tyrosine; kinases can use PLCγ as a substrate (Khare et al., 1997; Berridge, 1998; Harder et al., 1998). We found that GDNF-evoked long-lasting $Ca^{2+}$ elevation in $Ret^{-/-}$ neurons was significantly and reversibly inhibited by low doses of selective Src kinase inhibitor PP1 (FIG. 4A, 9 recorded neurons). In vitro kinase assay on anti-GFRα1-precipitated Triton X-100 insoluble lysate from GDNF-stimulated $Ret^{-/-}$ DRG neurons revealed a major phosphoprotein of approximately 60 kD (FIG. 4B), that corresponds to the Mr of several Src-type tyrosine kinases (p59 Fyn, pp60 Src and p62 Yes). These ~60 kD bands were absent in the control immunoprecipitation experiments (FIG. 4B).

We further checked the possibility of whether the activation of a GFRα1-coupled kinase would lead to phosphorylation of the serine/threonine kinases ERK1 and ERK2 (MAPK) in the absence of Ret, bearing in mind that Src kinases might activate MAPK (Dikic et al., 1996). Using antibodies which recognize phosphorylated MAPK we found that in DRG neurons isolated from E18 $Ret^{-/-}$ mice application of GDNF (100 ng/ml) evokes several-fold rapid activation of MAPK (n=3 experiments, FIG. 4C). Exposure of neurons to neurotrophins, such as BDNF, activates the Ras/ERK/pp90 ribosomal S6 kinase pathway that culminates in CREB phosphorylation (Finkbeiner et al., 1997). We found that CREB phosphorylation in Ser-133 increased substantially already at 5 min after GDNF treatment in $Ret^{-/-}$ DRG neurons (FIG. 4D).

Example 6

GDNF Simulates GFRα1-Coupled p62Yes Type Kinase in SHEP Neuroblastoma Cells

Figure 5A:
FIGS. 5 A–C depict GDNF-stimulated Src-type kinases associated with GFRα1 in the Ret negative human SHEP neuroblastoma cell line. A. RT-PCR analysis shows that SHEP cells express only GFRα1 (538 bp fragment), but not GFRα2 or Ret mRNA (expected fragments of 280 and 281 bp, correspondingly). The $H_2O$ control is as shown in FIG. 1C. B. Upper panel: the Triton X-100 insoluble fraction from the lysates of SHEP cells were immunoprecipitated (IP) with anti-GFRα1 antibodies and assayed for in vitro kinase activity as described in the Materials and Methods section. The cells were non-treated (0 min) or treated with 100 ng/ml GDNF for the time indicated. The optical density of the bands was determined using a phosphoimager and a TINA program and is presented as fold increase relative to control (GDNF non-treated cells). Lower panel: the precipitates after the kinase assay were probed by Western blotting (WB) with pan-Src antibodies, which recognize Fyn, Yes and Src. C. Left panel (GFRα1): the postnuclear lysate from SHEP cells non-treated (−) or pre-treated (+) with GDNF (100 ng/ml, 1 min) was precipitated with GFRα1 antibodies. Co-precipitates were assayed for kinase activity as described in Materials and Methods section. GDNF significantly increased Src type kinase activity associated with GFRα1. These results are representative of 5 independent experiments. Right panel (Yes): SHEP cells were not-treated (−) or pre-treated (+) with GDNF (100 ng/ml; 1 min), the Src-related kinase p62Yes was immunoprecipitated from the whole cell lysates (without preliminary IP with anti-GFRα1 antibody) with an anti-Yes polyclonal antibody and assayed for kinase activity. It revealed that the major GDNF-stimulated band co-migrates with Yes type kinase of about 62 kD. The samples were normalized by protein amount FIGS. 6 A–C depict GDNF-evoked phosphorylation of MAPK, CREB and ATF-1 in the Ret-negative: SHEP neuroblastoma cell line. A. Addition of GDNF evoked transient and profound increase of p42/p44 MAPK phosphorylation (left panel). The numbers below lane indicate the fold induction of p42 phosphorylation relative to control. Lower panel shows the re-probing of the same filter with anti-GFRα1 antibodies and demonstrates comparable amount of GFRα1 protein in all lanes. The results shown are representative of four independent experiments. B GDNF induced phosphorylation of p42/p44 MAPK was completely abolished by a 5-minute pretreatment with PP2 even at the low concentration, 1 μM (upper panel). The blot was re-probed with the anti-GFRα1 antibodies. Lower panel shows that GFRα1 protein was distributed equally in all lanes (n=2 experiments). C. GDNF treatment of SHEP cells resulted in potent induction of CREB Ser-133 phosphorylation as well as induced phosphorylation of the CREB-related protein ATF-1. The numbers below the lanes indicate the fold induction of CREB phosphorylation relative to control. The lower panel shows the re-probing of the same filter with anti-CREB antibodies (n=2 experiments).
Figure 5B:
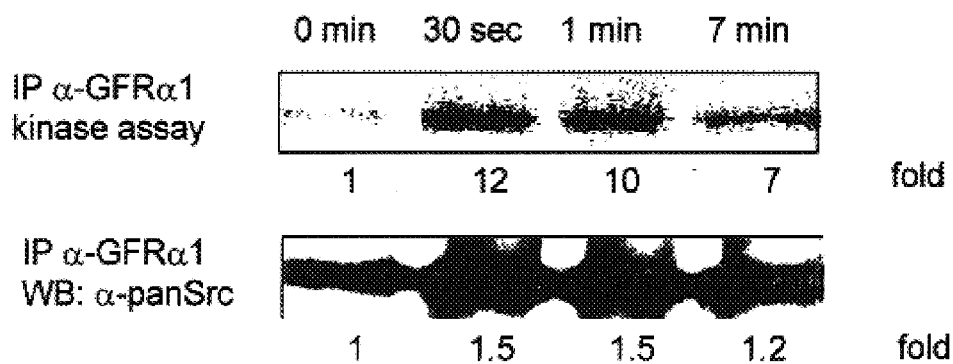
Figure 5C:
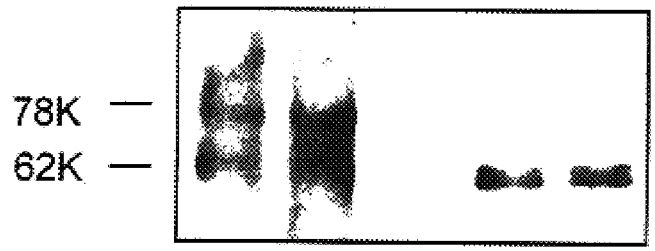

We used SHEP human neuroblastoma cells line for further exploration of GDNF-dependent non-Ret signaling. SHEP cells lack Ret mRNA but express GFRα1 mRNA (FIG. 5A) and an ample amount of GFRα1 protein (data not shown). On average in these cells, GDNF (100 ng/ml) evoked about a twelve-fold time-dependent increase of a Src-type kinase activity (FIG. 5B) as detected in co-precipitates with anti-GFRα1 antibodies from Triton X-100 insoluble fractions using a phosphoimager and a TINA program. To identify the particular Src-type kinase, activated by GDNF, we precipitated cell lysate with anti-Yes antibodies and performed the kinase assay thereafter. A major GDNF-stimulated kinase co-precipitated with GFRα1 co-migrate with p62Yes kinase (FIG. 5C). Another protein with Mr of about 72–75 kD was also co-precipitated with GFRα1 antibodies. The nature of this protein is unknown.

Example 7

GDNF Activates ERK1/ERK2, CREB and CREB-related Protein ATF-1 in SHEP Cell

Figure 6A:
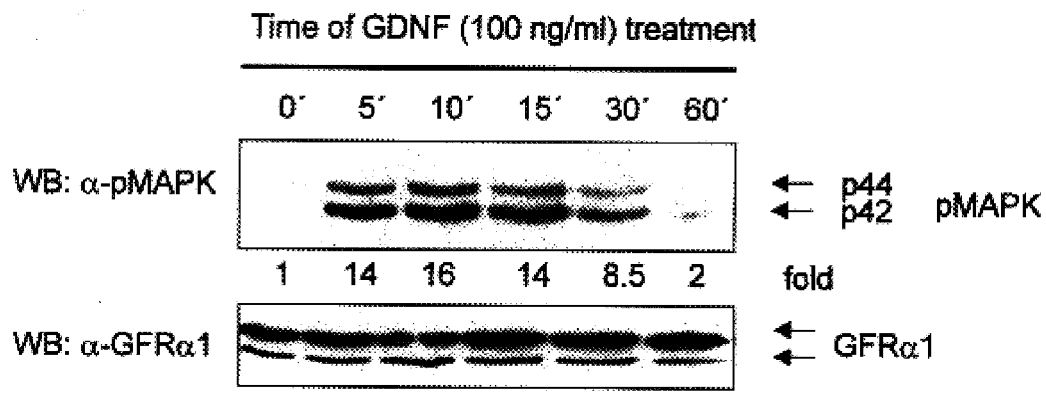
Figure 6B:
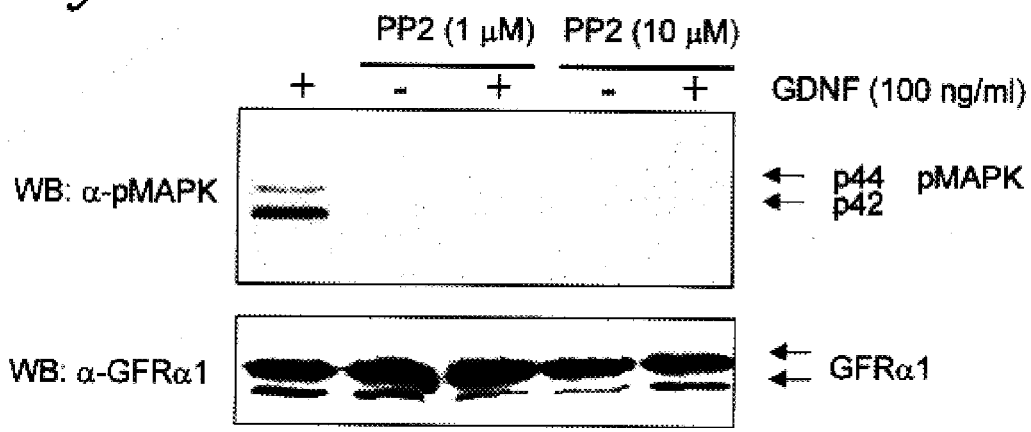

In SHEP cells application of GDNF (100 ng/ml) evoked a similar rapid MAPK activation as in $Ret^{-/-}$ DRG neurons (n=3 experiments, FIG. 6A, compare with FIG. 4C). This fast pattern of MAPK activation in $Ret^{-/-}$ E18 DRG neurons and in SHEP neuroblastoma cells is different from the long-lasting elevation of MAPK phosphorylation observed in Ret/GFRα1 expressing cells (Trupp et al., 1999). The GDNF-dependent phosphorylation of MAPK was almost completely blocked by Src-type Kinase inhibitor, PP2, already at a low concentration (1 μM) FIG. 6B exclude the possibility that PP2 affected other than Src type kinases, we checked the effect of PP2 on NGF-mediated MAPK activation in PC12 cells. PP2 (0.1–10 μM) did not affect NGF-dependent activation of MAPK in PC12 (data not shown).

Figure 6C:
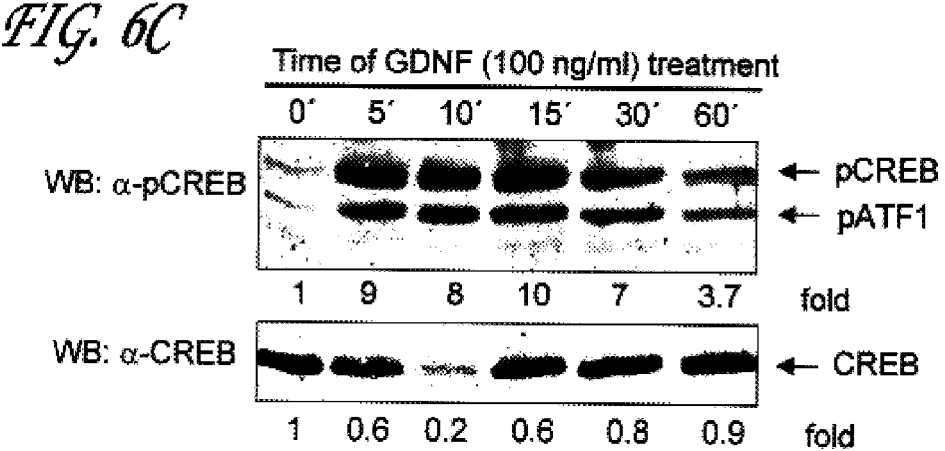

We further investigated whether GDNF affects phosphorylation of CREB and we found that GDNF potently induced phosphorylation of CREB in Ser-133 site (FIG. 6C, n=2 experiments). Interestingly, GDNF also induced phosphorylation of the CREB-related protein ATF-1 (FIG. 6C). The dynamics of GDNF-induced Ret-independent CREB and ATF-1 phosphorylation was similar to that of GDNF-induced MAPK phosphorylation.

Example 8

Figure 7A:
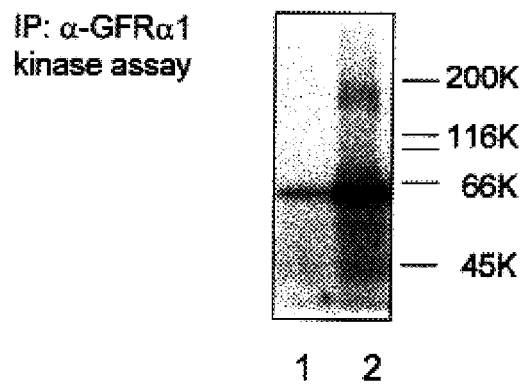
FIGS. 7 A–C depict GDNF-activated Src type kinase and MAP kinase in NIH 3T3 fibroblasts stably tansfected with GFRα1. A. The kinase assay experiments. The major ~60 kD proteins can be co-precipitated with GFRα1 after GDNF (100 ng/ml) pre-treatment both in Neuro2A-20 neuroblastoma cells expressing Ret (1) and in the NIH3T3 fibroblast cells (2) (both cell lines were stably transfected with GFRα1). B. GDNF induced phosphorylation of p42/p44 MAPK in NIH 3T3 cells lacking Ret (upper panel; n=3 independent experiments). Pre-treatment of the cells with selective Src kinase inhibitor, PP2 (5 μM) for the indicated time abolished the effect of GDNF. The numbers below lanes indicate fold induction of p42 MAPK phosphorylation relative to control. The lower panel shows a reprobing of the same filter with anti-GFRα1 antibodies and demonstrates comparable amounts of GFRα1 protein in all lanes (n=2 independent experiments). C. Neuro2A neuroblastoma cells expressing Ret but not endogenous GFRα1 was treated with GDNF in the presence of a soluble GFRα1 (GFRα1/Fc chimeric protein; 1 μg/ml) lacking a GPI anchor. Soluble GFRα1 induced GDNF-dependent phosphorylation of p42/p44 MAPK. The numbers below lanes indicate fold induction of p42 MAPK phosphorylation relative to control (non-treated with GDNF).
Figure 7B:
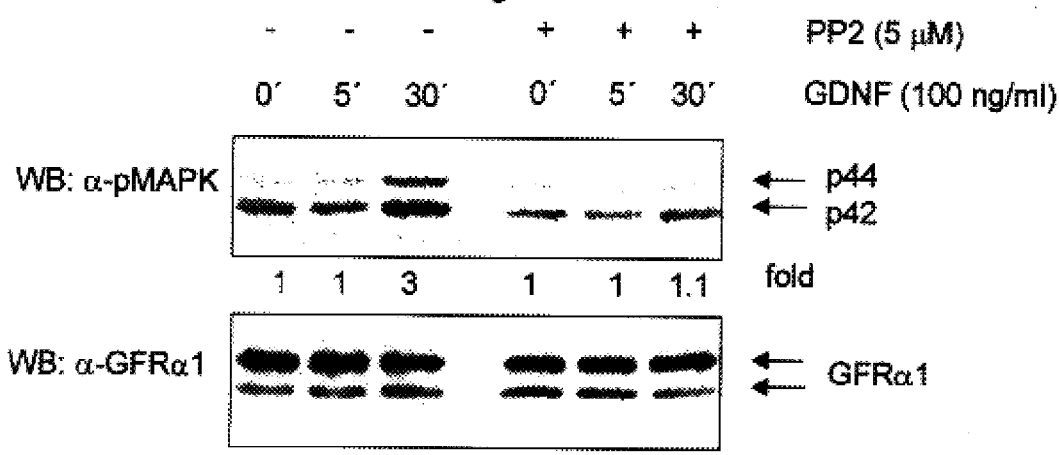
Figure 7C:
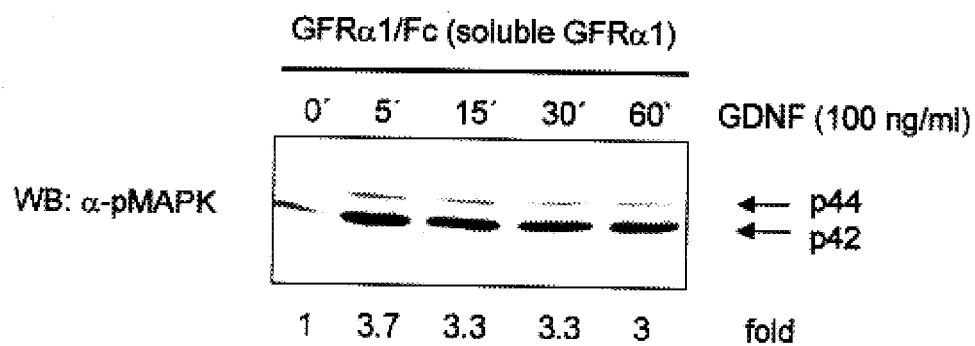

GDNF Induces Activation of ERK1/ERK2 in NIH 3T3 Fibroblasts Via Src Type Kinases NIH 3T3 fibroblasts stably tansfected with GFRα1 (NIH3T3/pBpGFRα1) do not express Ret and were therefore used as a non-neuronal cell line for investigating the GDNF-evoked Ret-independent signaling. Src-type kinases can be also co-precipitated with GFRα1 antibodies in these cells (n=2 experiments; FIG. 7A). GDNF (100 ng/ml) again reproducibly increased phosphorylation of MAPK in 3T3NIH/pBpGFRα1 fibroblasts (n=3 experiments, FIG. 7B), although the MAPK activation was delayed in comparison with a rapid activation in $Ret^{-/-}$ DRG neurons and in SHEP neuroblastoma cells. Application of PP2 (5 μM) again eliminated GDNF-evoked MAPK phosphorylation in 3T3NIH/pBpGFRα1 cells (FIG. 7B, right panel, n=2 experiments). In parental NIH3T3 fibroblasts lacking both Ret and GFRα1 the application of GDNF (100 ng/ml) either alone or together with a soluble GFRα1 (GFRα1/Fc lacking GPI anchor; 1 μg/ml) did not evoke any MAPK phosphorylation (data not shown). In the presence of GDNF the soluble GFRα1 was able to phosphorylate MAPK in Neuro2A neuroblastoma cells lacking endogenous GFRα1 but expressing Ret (FIG. 7C).

Example 9

GDNF Transiently Activates PLCγ but not JNK in SHEP Cell

Figure 8A:
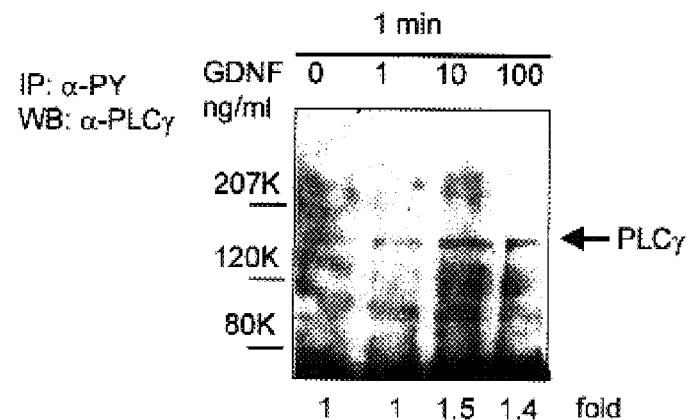
FIGS. 8 A–C depict GDNF-increased PLCγ tyrosine phosphorylation in SHEP neuroblastoma cells. A. SHEP cells were incubated with the indicated concentrations of GDNF for 1 min, and then lysed. Tyrosine-phosphorylated proteins were immunoprecipitated with 4G-10 anti-phosphotyrosine antibodies (α-PY) and than probed for PLCγ with anti-PLCγ antibodies by Western blotting as described in the Materials and Methods. GDNF evoked a dose-dependent increase in PLCγ tyrosine phosphorylation (n=3 experiments). The samples were normalized by protein amount. B. Left panel: SHEP cells were incubated with indicated concentrations of GDNF for 1 min or for 5 min. PLCγ proteins were immunoprecipitated from the lysates by anti-PLCγ antibodies. The immunocomplexes were probed for tyrosine-phosphorylated proteins with 4G-10 antibodies (α-PY) by Western blotting. Right panel: the blot was re-probed with anti-PLCγ antibodies. In all panels the numbers below lanes indicate fold induction of PLCγ phosphorylation relative to control. C. GDNF application did not affect the phosphorylation of JNK (n=2 experiments).
Figure 8B:
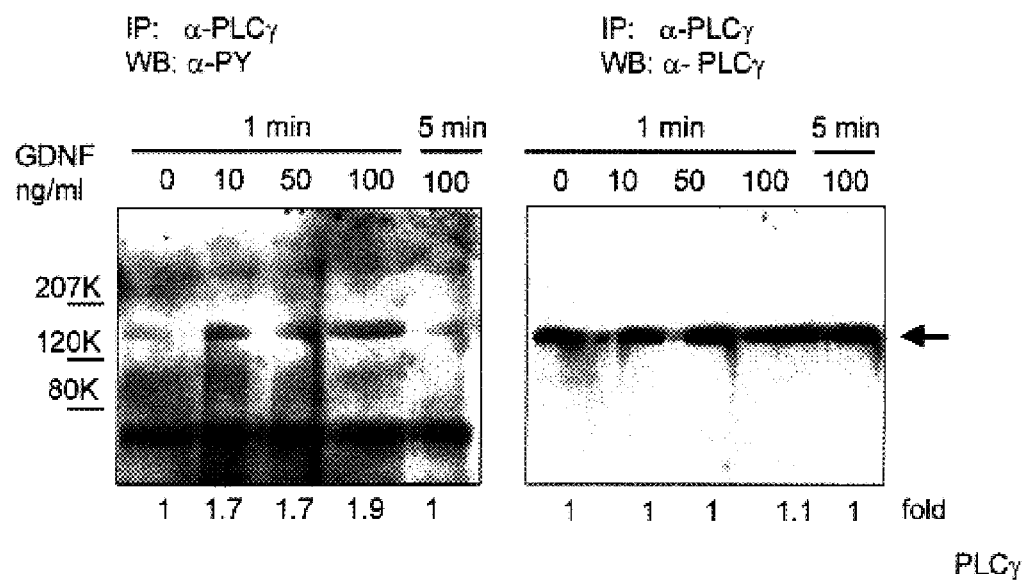
Figure 8C:
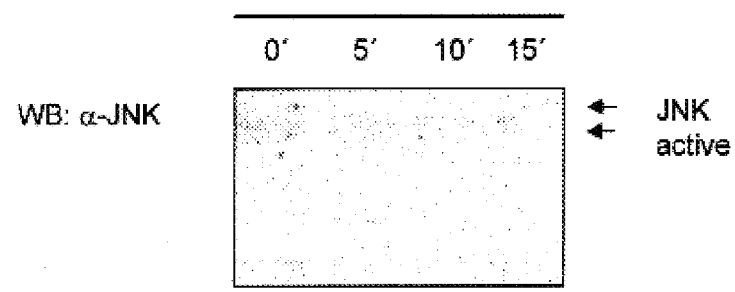

We investigated further whether GDNF can trigger PLCγ activation in SHEP cells. Treatment of SHEP neuroblastoma cells with GDNF (1–100 ng/ml) significantly increased PLCγ tyrosine phosphorylation (n=3 experiments, FIG. 8A). The effect was fast, with a significant increase at 1 min, and a return to basal tyrosine phosphorylation levels within 5 min (FIG. 8B). It has been shown that activation of endogenous Ret in PC12 cells as well as activation of transiently or stably expressed Ret in COS-1 cells or NIH3T3 fibroblasts leads to the phosphorylation of c-Jun NH2-terminal protein kinase (JNK) (Chiariello et al., 1998). In our experiments GDNF (100 ng/ml) did not evoke JNK activation in SHEP cells lacking Ret (n=2 experiments; FIG. 8C).

The foregoing examples are meant to illustrate the invention and are not to be construed to limit the invention in any way. Those skilled in the art will recognize modifications that are within the spirit and scope of the invention.

REFERENCES

All references cited herein are hereby incorporated by reference in their entireties.

Airaksinen, M. S., Titievsky, A. and Saarma, M. (1999) GDNF family neurotrophic factor signaling: four masters, one servant? *Molecular and Cellular Neuroscience*, 13,313–325.

Arénas, E., Trupp, M., Åkerud, P. and Ibañéz, C. F. (1995) GDNF prevents degeneration and promotes the phenotype of brain noradrenergic neurons in vivo. *Neuron*, 1465–1473.

Baloh, R. H., Tansey, M. G., Lampe, P. A., Fahrner, T. J., Enomoto, H., Simburger, K. S., Leitner, M. L., Araki, T., Johnson, E. M. J. and Milbrandt, J. (1998) Artemin, a novel member of the GDNF ligand family, supports peripheral and central neurons and signals through the GFRα3-RET receptor complex. *Neuron*, 21, 1291–1302.

Beck, K. D., Valverde, J., Alexi, T., Poulsen, K., Moffat, B., Vandlen, R. A., Rosenthal, A. and Hefti, F. (1995) Mesencephalic dopaminergic neurons protected by GDNF from axotomy-induced degeneration in the adult brain. *Nature*, 373, 339–341.

Berridge, M. J. (1998) Neuronal calcium signaling. *Neuron*, 21, 13–26.

Borrello, M. G., Alberti, L., Arighi, E., Bongarzone, I., Battistini, C., Bardelli, A., Pasini, B., Piutti, C., Rizzetti, M. G., Mondellini, P., Radice, M. T. and Pierotti, M. A. (1996) The full oncogenic activity of Ret/ptc2 depends on tyrosine 539, a docking site for phospholipase Cgamma. *Molecular & Cellular Biology*, 16, 2151–2163.

Bourette, R. P., Myles, G. M., Choi, J. L. and Rohrschneider, L. R. (1997) Sequential activation of phosphatidylinositol 3-kinase and phospholipase C-gamma2 by the M-CSF receptor is necessary for differentiation signaling. *EMBO Journal*, 16, 5880–5893.

Brown, D. A. and London, E. (1998) Functions of lipid rafts in biological membranes. *Annual Review of Cell Developmental Biology*, 14, 111–136.

Buj-Bello, A., Buchman, V. L., Horton, A., Rosenthal, A. and Davies, A. M. (1995) GDNF is an age-specific survival factor for sensory and autonomic neurons. *Neuron*, 15, 821–828.

Buj-Bello, A., Adu, J., Pinon, L. G. P., Horton, A., Thompson, I., Rosenthal, A., Chinchetru, M., Buchman, V. L. and Davies, A. M. (1997) Neurturin responsiveness requires a GPI-anchored receptor and the Ret receptor tyrosine kinase. *Nature*, 387, 721–724.

Cacalano, G., Fariñas, I., Wang, L. C., Hagler, K., Forgie, A., Moore, M., Armanini, M., Phillips, H., Ryan, A. M., Reichardt, L. F., Hynes, M., Davies, A. and Rosenthal, A. (1998) GFRα1 is an essential receptor component for GDNF in the developing nervous system and kidney. *Neuron*, 21, 53–62.

Chiariello, M., Visconti, R., Carlomagno, F., Melillo, R. M., Bucci, C., de Franciscis, V.:, Fox, G. M., Jing, S., Coso, O. A., Gutkind, J. S., Fusco, A. and Santoro, M. (1998) Signaling of the Ret receptor tyrosine kinase through the c-Jun NH$_2$-terminal protein kinase (JNKS): evidence for a divergence of the ERKs and JNKs pathways induced by Ret. *Oncogene*, 16, 2435–2445.

Davletov, B. A., Meunier, F. A., Ashton, A. C., Matsushita, H., Hirst, W. D., Lelianova, V. G., Wilkin, G. P., Dolly, J. O. and Ushkaryov, Y. A. (1998) Vesicle exocytosis stimulated by alpha-latrotoxin is mediated by latrophilin and requires both external and stored $Ca^{2+}$. *EMBO Journal* 17, 3909–3920.

Dikic, I., Tokiwa, G., Lev, S., Courtneidge, S. A. and Schiessinger, J. (1996) A role for Pyk2 and Src in linking G-protein-coupled receptors with MAP kinase activation. *Nature*, 383, 547–550.

Durbec, P., Marcos-Gutierrez, C. V., Kilkenny, C., Grigoriou, M., Wartiowaara, K., Suvanto, P., Smith, D., Ponder, B., Constantini F., and Saarma, M. et al. (1996) GDNF signaling through the Ret receptor tyrosine kinase. *Nature*, 381, 789–793.

Enomoto, H., Araki, T., Jackman, A., Heuckeroth, R. O., Snider, W. D., Johnson, EM., Jr. and Milbrandt, J. (1998) GFR alpha1-deficient mice have deficits in the enteric nervous system and kidneys. *Neuron*, 21, 317–324.

Finkbeiner, S., Tavazoie, S. F., Maloratsky, A., Jacobs, K. M., Harris, K. M. and Greenberg, M. E. (1997) CREB: A major mediator of neuronal neurotrophin responses. *Neuron*, 19, 1031–1047.

Finkbeiner, S. and Greenberg, M. E. (1998) $Ca^{2+}$ channel-regulated neuronal gene expression. *Journal of Neurobiology*, 37, 171–189.

Friedrichson, T. and Kurzchalia, T. V. (1998) Microdomains of GPI-anchored proteins in living cells revealed by crosslinking. *Nature*, 394, 802–805.

Fukunaga, K. and Miyamoto, E. (1998) Role of MAP kinase in neurons. *Molecular Neurobilogy*, 16, 79–95.

Ghosh, A. and Greenberg, M. E. (1995) Calcium signaling in neurons: molecular mechanisms and cellular consequences. *Science*, 268,239–247.

Golden, J. P., DeMaro, J. A., Osborne, P. A., Milbrandt, J. and Johnson, E. M. Jr. (1999) Expression of neurturin, GDNF, and GDNF family-recptor mRNA in the developing and mature mouse. *Experimental Neurology*, 58, 504–528.

Green, J. M., Schreiber, A. D. and Brown, E. J. (1997) Role for a glycan phosphoinositol ;anchor in (Fed. Cir. gamma receptor synergy. *Journal of Cell Biology*, 139, 1209–1217.

Harder, T., Scheiffele, P., Verkade, P. and Simons, K. (1998) Lipid domain structure of the plasma membrane revealed by patching of membrane components. *Journal of Cell Biology*, 141, 929–942.

Henderson, C. E., Phillips, H. S., Pollock, K. A., Davies, A. M., Lemeulle, C., Armanini, M, Simmons, L., Moffet, B., Vandlen, K. A., Simpson, L. C., Simmons, L. and et al. (1994) GDNF: a potent survival factor for motoneurons present in peripheral nerve and muscle. *Science*, 266, 1062–1064.

Hishiki; T., Nimura, Y., Isogai, E., Kondo, K., Ichimiya, S., Nakamura, Y., Ozaki, T., Sakiyama, S., Hirose, M., Seki, N., Takahashi, H., Ohnuma, N., Tanabe, M. and Nakagawara, A. (1998) Glial cell line-derived neurotrophic factor/neurturin-induced differentiation and its enhancement by retinoic acid in primary human neuroblastomas expressing c-Ret, GFR alpha-1, and GFR alpha-2. *Cancer Research*, 58, 2158–2165.

Impey, S., Obrietan, K. and Storm, D. R. (1999) Making new connections: role of ERK/MAP kinase signaling in neuronal plasticity. *Neuron*, 23, 11–14.

Jiang, H. and Guroff, G. (1997) Actions of the neurotrophins on calcium uptake. *Journal of Neuroscience Research*, 50, 355–360.

Jing, S. Q., Wen, D. Z., Yu, Y. B., Holst, P. L., Luo, Y., Fang, M., Tamir, A, Antonio, L, Hu, Z., Cupples, R., Louis, J. C., Hu, S., Altrock, B. W. and Fox, G. M. (1996) GDNF-induced activation of the Ret protein tyrosine kinase is mediated by GDNFR-alpha, a novel receptor for GDNF. *Cell*, 85, 1113–1124.

Jing, S., Yu, Y., Fang, M., Hu, Z., Holst, P. L., Boone, T., Delaney, J., Schultz, H., Zhou, R. and Fox, G. M. (1997) GFRα-2 and GFRα-3 are two new receptors for ligands of the GDNF family. *Journal of Biological Chemistry*, 272, 33111–33117.

Khlare, S., Bolt, M. J., Wali, R. K., Skarosi, S. F., Roy, H. K., Niedziela, S., Scaglione-Sewell, B., Aquino, B., Abraham, C., Sitrin, M. D., Brasitus, T. A. and Bissonnette, M. (1997) 1,25 dihydroxyvitamin D3 stimulates phospholipase C-gamma in rat colonocytes: role of c-Src in PLC-gamma activation. *Journal of Clinical Investigation*, 99, 1831–1841.

Klein, R. D., Sherman, D., Ho, W. H., Stone, D., Bennett, G. L., Moffat, B., Vandlen, R., Simmons, L., Gu, Q., Hongo, J. A. et al. (1997) A GPI-linked protein that interacts with Ret to form a candidate neurturin receptor. *Nature*, 387, 717–721.

Kokaia; Z., Airaksinen, M. S., Nanobashvili, A., Larsson, E., Kujamäki, E., Lindvall, O. and Saarma, M. (1999) GDNF family ligands and receptors are differentially regulated after brain insults in the rat. *European Journal of Neuroscience*, 11, 1202–1216.

Kotzbauer, P. T., Lampe, P. A., Heuckeroth, R. O., Golden, J. P., Creedon, D. J., Johnson, EM J and Milbrandt, J. (1996) Neurturin, a relative of glial-cell-line-derived neurotrophic factor. *Nature*, 384, 467470.

Lang, D. M., Lommel, S., Jung, M., Ankerhold, R., Petrausch, B., Laessing, U., Wiechers, M. F., Plattner, H. and Stuermer, C. A. O. (1998) Identification of reggie-1 and reggie-2 as plasmamembrane-associated proteins which cocluster with activated GPI-anchored cell, adhesion molecules in non-caveolar micropatches in neurons. *Journal of Neurobiology*, 37, 502–523.

Lin, L. F., Doherty, D. H., Lile, J. D., Bektesh, S. and Collins, F. (1993) GDNF: a glial cell line-derived neurotrophic factor for midbrain dopaminergic neurons. *Science*, 260, 1130–1132.

Luttrell, L. M., Hawes, B. E., van Biesen, T., Luttrell, D. K., Lansing, T. J., Lefkowitz, R. J. (1996) Role of c-Src tyrosine kinase in G protein-coupled receptor—and Gbeta-gamma subunit-mediated activation of mitogen-activated protein kinases. *Journal of Biological Chemistry*, 271, 19443–19450.

Luttrell, L. M., Daaka, Y., Della Rocca, G. J. and Lefkowitz, R. J. (1997) G protein-coupled receptors mediate two functionally distinct pathways of tyrosine phosphorylation in rat 1a fibroblasts. Shc phosphorylation and receptor endocytosis correlate with activation of Erk kinases. *Journal of Biological Chemistry*, 272, 31648–31656.

Luttrell, L. M., Ferguson, S. S. G., Daaka, Y., Miller, W. E., Maudsley, S., Della Rocca, G. J., Lin, F. -T., Kawakatsu, H., Owada, K., Luttrell, D. K., Caron, M. G. and Lefkowitz, R. J. (1999) β-arrestin-dependent formation of $\beta_2$ adrenergic receptor-Src protein kinase complexes. *Science*, 283, 655–661.

Meyer zu Heringdorf D., Lass H., Alemany R., Laser K. T., Neumann E., Zhang C., Schmidt M., Rauen U., Jakobs K. H., van Koppen C. J. (1998) Sphingosine kinase-mediated $Ca^{2+}$ signaling by G-protein-coupled receptors. *EMBO Journal*, 17, 2830–2837.

Milbrandt, J., de Sauvage, F. J., Fahrner, T. J., Baloh, R. H., Leitner, M. L., Tansey, MG, Lampe, P. A., Heuckeroth, R. O., Kotzbauer, P. T., Simburger, K. S., Golden, J. P., Davies, J. A., Vejsada, R., Kato, A. C., Hynes, M., Sherman, D., Nishimura, M., Wang, L C, Vandlen, R;, Moffat, B., Klein, R. D., Poulsen, K., Gray, C., Garces, A. and Johnson, E. M. J. (1998) Persephin, a novel neurotrophic factor related to GDNF and neurturin. *Neuron*, 20, 245–253.

Moore, M. W., Klein, R. D., Farinas, I., Sauer, H., Armanini, M., Phillips, H., Reichardt, L. F., Ryan, A. M., Carver-Moore, K. and Rosenthal, A. (1996) Renal and neuronal abnormalities in mice lacking GDNF. *Nature*, 382, 76–79.

Natarajan, D., Grigoriou, M., Marcos-Gutierrez, C. V., Atkins, C. and Pachnis, V. (1999) Multipotential progenitors of the mammalian enteric nervous system capable of colonising aganglionic bowel in organ culture. *Development*, 126, 157–168.

Oppenheim, R. W., Houenou, L. J., Johnson, J. E., Lin, L. F., Li, L., Lo, A. C., Newsome, AL, Prevette, D. M. and Wang, S. (1995) Developing motor neurons rescued from programmed and axotomy—induced cell death by GDNF. *Nature*, 373, 344–346.

Pichel, J. G., Shen, L., Sheng, H. Z., Granholm, A. C., Drago, J., Grinberg, A., Lee, EJ, Huang, S. P., Saarma, M., Hoffer, B. J., Sariola, H. and Westphal, H. (1996) Defects in enteric innervation and kidney development in mice lacking GDNF. *Nature*, 382, 73–76.

Rossi, J., Luukko, K., Poteryaev, D., Laurikainen, A., Sun, Y. F., Laakso, T., Eerikäinen, S., Tuominen, R., Lakso, M., Rauvala, H., Arumäe, U., Pasternack, M., Saarma, M. and Airaksinen, M. S. (1999) Retarded growth and deficits in the enteric and parasympathetic nervous system in mice lacking GFRα2, a functional neurturin receptor. *Neuron*, 22, 243–252.

Saarma, M. and Sariola, H. (1999) Other neurotrophic factors: glial cell line-derived neurotrophic factor (GDNF). *Microscopy Research Techniques*, 45, 292–302.

Sanicola, M., Hession, C., Worley, D., Carmillo, P., Ehrenfels, C., Walus, L., Robinson, S., Jaworski G., Wei, H., Tizard, R., Whitty, A., Pepinsky, R. B. and Cate, R. L. (1997) Glial cell line-derived neurotrophic factor-dependent RET activation can be mediated by two different cell-surface accessory proteins. *Proc. Nat. Acad. Sci. USA*, 94, 6238–6243.

Sánchez, M. P., Silos-Santiago, I., Frisen, J., He, B., Lira, S. A. and Barbacid, M. (1996) Renal agenesis and the absence of enteric neurons in mice lacking GDNF. *Nature*, 382, 70–73.

Sargiacomo, M., Sudol, M., Tang, Z. and Lizanti, M. P. (1993) Signal transducing molecules and glycosyl-phosphatidylinositol-linked proteins form a caveolin-rich insoluble complex in MDCK cells. *Journal of Cell Biology*, 122, 789–807.

Schuchardt, A., D'Agati, V., Larsson-Blomberg, L., Costantini, F. and Pachnis, V. (1994) Defects in the kidney and enteric nervous system of mice lacking the tyrosine kinase receptor Ret. *Nature*, 367, 380–383.

Sharenberg, A. M. and Kinet, J. -P. (1998) PtdIns-3,4,5-P3: a regulatory nexus between tyrosin e kinases and sustained calcium signals. *Cell*, 94, 5–8.

Simons, K. and Ikonen, E. (1997) Functional rafts in cell membranes. *Nature*, 387, 569–572.

Stam, J. C., Michiels, F., van der Kammen, R. A., Moolenaar, W. H. and Collard, J. G. (1998) Invasion of T-lymphoma cells cooperation between Rho family GTPases and lysophospholipid receptor signaling. *EMBO Journal*, 17, 4066–74.

Suvanto, P., Wartiovaara, K., Lindahl, M., Arumäe U., Moshnyakov, M., Horelli-Kuitunen, N., Airaksinen, M. S., Palotie, A., Sariola, H. and Saarma, M. (1997) Cloning, mRNA distribution and chromosomal localisation of the gene for glial cell line-derived neurotrohic factor receptor β, a homologue to GDNFR-α. *Human Molecular Genetics*, 6, 1267–1273.

Takei, K., Shin, R. M., Inoue, T., Kato, K. and Mikoshiba, K. (1998) Regulation of nerve growth mediated by inositol 1,4,5-trisphosphate receptors in growth cones. *Science*, 282, 1705–1708.

Taraviras, S., Marcos-Gutierrez, C. V., Durbec, P., Jani, H., Grigoriou, M., Sukumaran, M., Wang, L. C. Hynes, M., Raisman, G. and Pachnis, V. (1999) Signaling by the RET receptor tyrosine kinase and its role in the development of the mammalian enteric nervous system. *Development*, 126, 2785–2797.

Thomas, S. M. and Brugge, J. S. (1997) Cellular functions regulated by Src family kinases. *Annual Review of Cell & Developmental Biology*, 13, 513–609.

Thorn, P., Lawrie, A. M., Smith, P. M., Gallacher, D. V. and Petersen, O. H. (1993) Local and global cytosolic $Ca^{2+}$ oscillations in exocrine cells evoked by agonists and inositol trisphosphate. *Cell*, 74, 661–668.

Tomac, A., Lindqvist, E., Lin, L. F., Ogren, S. O., Young, D., Hoffer, B. J. and Olson, L. (1995) Protection and repair of the nigrostriatal dopaminergic system by GDNF in vivo *Nature*, 373, 335–339.

Treanor, J. J., Goodman, L., de Sauvage, F., Stone, D. M., Poulsen, K. T., Beck, C. D., Gray, C., Armanini, M. P., Pollock, R. A., Hefti, F., Phillips, H. S., Goddard, A., Moore, M. W., Buj-Bello, A., Davies, A. M., Asai, N., Takahashi, M., Vandlen, R, Henderson, C. E. and Rosenthal, A. (1996) Characterization of a multicomponent receptor for GDNF. *Nature*, 382, 80–83.

Trupp, M., Ryden, M., Jörnvall, H., Funakoshi, H., Timmusk, T., Arenas, E. and Ibañéz, C. F. (1995) Peripheral expression and biological activities of GDNF, a new neurotrophic factor for avian and mammalian peripheral neurons. *Journal of Cell Biology*, 130, 137–148.

Trupp, M., Arenas, E., Fainzilber, M., Nilsson, A. S., Sieber, B. A., Grigoriou, M., Kilkenny, C., Salazar-Grueso, E., Pachnis, V., Arumäe, U., Sariola, H., Saarma, M. and Ibañéz, C. F. (1996) Functional receptor for GDNF encoded by the c-ret proto-oncogene. *Nature*, 381, 785–788.

Trupp, M., Belluardo, N., Funakoshi, H., Ibañéz, C. F. (1997) Complementary and overlapping expression of glial cell line- derived neurotrophic factor (GDNF), c-Ret proto-oncogene, and GDNF receptor-alpha indicates multiple mechanisms of trophic actions in the adult rat CNS. *Journal of Neuroscience*, 17, 3554–3567.

Trupp, M., Scott, R., Whittemore, S. R. and Ibañéz, C. F. (1999) Ret-dependent and—independent mechanisms of glial cell line-derived neurotrophic factor signaling in neuronal cells. *Journal of Biological Chemistry*, 274, 20885–20894.

Usachev, Y. M. and Thayer, S. A. (1999) $Ca^{2+}$ influx in resting rat sensory neurones that regulates and is regulated by ryanodine-sensitive $Ca^{2+}$ stores. *Journal of Physiology*, 519, 115–130.

Varma,. R. and Mayor, S. (1998) GPI-anchored proteins are organized in submicron domains at the cell surface. *Nature*, 394, 798–801.

Viola, A., Schroeder, S., Sakakibara, Y. and Lanzavecchia, A. (1999) T lymphocyte costimulation mediated by reorganization of membrane microdomains. *Science*, 283, 680–682.

Yan, Q., Matheson, C. and Lopez, O. T. (1995) In vivo neurotrophic effects of GDNF on neonatal and adult facial motor neurons. *Nature*, 373, 341–344.

Ylikoski, J., Pirvola, U., Virkkala, J., Suvanto, P., Liang, X. -Q., Magal, E., Altschuler, R., Miller, J. M. and Saarma, M. (1998) Guinea pig auditory neurons are protected by glial cell line-derived growth factor from degeneration after noise trauma *Hearing Research*, 124,17–26.

Yu, T., Scully, S., Yu, Y., Fox, G. M., Jing, S. and Zhou, R. (1998) Expression of GDNF family receptor components during development: implications in the mechanisms of interaction. *Journal of Neuroscience*, 18, 4684–4696.

What is claimed is:

1. A method for identifying a compound that is a agonist of Ret-independent intracellular signaling effected by GPI-anchored receptors in nervous system cells comprising (i) incubating nervous system cells expressing GPI-anchored receptors, but not Ret, with a test compound and (ii) determining whether intracellular signaling has been effected in said cells, thereby identifying a compound that is an agonist of Ret-independent intracellular signaling effected by said GPI-anchored receptors.

2. The method of claim 1, wherein said nervous system cells express GFRα receptors, but not Ret receptors.

3. The method of claim 2, wherein said GFRα receptors are GFRα receptors.

4. The method of claim 1, wherein said nervous system cells arc DRG neurons.

5. The method of claim 4, wherein said DRG neurons are Ret (−/−).

6. The method of claim 1, wherein said nervous system cells are neuroblastoma cells.

7. The method of claim 1, wherein said intracellular signaling is measured as an increase in intracellular $Ca^{2+}$ concentration as compared to controls not incubated with said compound.

8. The method of claim 7 further comprising determining that said test compound binds to said GPI-anchored receptors.

9. The method of claim 1, wherein said intracellular signaling is measured as kinase activation.

10. The method of claim 9, wherein said kinase activation is measured by (i) preparing a cell lysate, (ii) immunoprecipitating the cell lysate with an anti-GPI-anchored receptor antibody to form an imnmunoprecipitate, (ii) performing an assay to measure kinase phosphorylation on said immunoprecipitate, and (iv) comparing the results with controls not incubated with said compound.

11. The method of claim 10, wherein said antibody is anti-GFRα1.

12. The method of claim 9, wherein said kinase is a Src-type kinase.

13. The method of claim 12, wherein activation of Src-type kinase is measured as activation of MAPK.

14. The method of claim 12, wherein activation of Src-type kinase is measured as activation of CREB.

15. The method of claim 12, wherein activation of Src-type kinase is measured as PLCγ activation.

16. A method for identifying a compound that is an antagonist of Ret-independent intracellular signaling effected by GPI-anchored receptors in nervous system cells comprising (i) incubating nervous system cells expressing GPI-anchored receptors, but not Ret, with a test compound in the presence of a sufficient amount of an agonist of said Ret-independent intracellular signaling to effect intracellular signaling, and (ii) comparing the results to controls not incubated with said compound, thereby identifying a compound that is an antagonist of Ret-independent intracellular signaling effected by GPI-anchored receptors.

17. The method of claim 16, wherein said nervous system cells express GFRα receptors.

18. The method of claim 17, wherein said GFRα receptors are GFRα1 receptors.

19. The method of claim 16, wherein said nervous system cells are DRG neurons.

20. The method of claim 19, wherein said DRG neurons are Ret (−/−).

21. The method of claim 16, wherein said nervous system cell are neuroblastoma cells.

22. The method of claim 16, wherein the intracellular signaling being measured is an increase intracellular $Ca^{2+}$ concentration.

23. The method of claim 16, wherein the intracellular signaling being measured is kinase activation.

24. The method of claim 23, wherein said kinase activation is measured by (i) preparing a cell lysate, (ii) immunoprecipitate the cell lysate with an anti-GPI-anchored receptor antibody to form an immunoprecipitate, (iii) performing an assay to measure kinase phosphorylation on said immunoprecipitate, and (iv) comparing the results with controls not incubated with said compound.

25. The method of claim 24, wherein said antibody is anti-GFRα1.

26. The method of claim 23, wherein said kinase is a Src-type kinase.

27. The method of claim 26, wherein said Src-type kinase activation is measured as activation of MAPK.

28. The method of claim 26, wherein said Src-type kinase activation is measured as CREB activation.

29. The method of claim 26, wherein said Src-type kinase activation is measured as PLCγ activation.

30. A method for identifying a compound that is an agonist of GFRα1-dependent, Ret-independent intracellular signaling comprising (i) incubating cells that express GFRα1 receptor, but not Ret receptor, with a test compound and (ii) determining whether intracellular signaling has been effected in said cells, thereby identifying a compound that is an agonist of GFRα1-dependent, Ret-independent intracellular signaling.

31. The method of claim 30, wherein said intracellular signaling is measured as an increase in intracellular $Ca^{2+}$ concentration as compared to controls not incubated with said compound.

32. The method of claim 31 further comprising determining that said test compound binds to said GPI-anchored receptors.

33. The method of claim 30, wherein said intracellular signaling is measured as kinase activation.

34. The method of claim 33, wherein said kinase activation is measured by (i) preparing a cell lysate, (ii) immunoprecipitating the detergent insoluble fraction of the cell lysate with an anti-GFRα1 receptor antibody to form an immunoprecipitate, (iii) performing an essay to measure kinase phosphorylation on said immunoprecipitate, and (iv) comparing the results with controls not incubated with said compound.

35. The method of claim 33, wherein said kinase is a Src-type kinase.

36. The method of claim 33, wherein activation of Src-type kinase is measured as activation of MAPK.

37. The method of claim 33, wherein activation of Src-type kinase is measured as activation of CREB.

38. The method of claim 33, wherein activation of Src-type kinase is measured as PLCγ activation.

39. A method for identifying a compound that is an antagonist of GFRα1-dependent, Ret-independent intracellular signaling comprising (i) incubating cells that express GFRα1 receptor, but not Ret receptor; with a test compound in the presence of a sufficient amount of an agonist of said intracellular signaling to effect intracellular signaling, and (iii) comparing the results to controls not incubated with said compound, thereby identifying a compound that is an antagonist of GFRα1-dependent, Ret-independent intracellular signaling.

40. The method of claim 39, wherein said agonist is GDNF.

41. The method of claim 39, wherein said intracellular signaling is measured as an increase in intracellular $Ca^{2+}$ concentration as compared to controls not incubated with said compound.

42. The method of claim 39 further comprising determining that said test compound binds to said GPI-anchored receptors.

43. The method of claim 39, wherein said intracellular signaling is measured as kinase activation.

44. The method of claim 43, wherein said kinase activation is measured by (i) preparing a cell lysate, (ii) immunoprecipitating the detergent insoluble fraction of the cell lysate with an anti-GFRα1 receptor antibody to form an immunoprecipitate, (iii) performing an assay to measure kinase phosphorylation on said immunoprecipitate, and (iv) comparing the results with controls not incubated with said compound.

45. The method of claim 43, wherein said kinase is a Src-type kinase.

46. The method of claim 43, wherein activation of Src-type kinase is measured as activation of MAPK.

47. The method of claim 43, wherein activation of Src-type kinase is measured as activation of CREB.

48. The method of claim 43, wherein activation of Src-type kinase is measured as PLCγ activation.

49. A method for identifying a compound which is an agonist of GFRα1 independent, Ret-independent intracellular signaling comprising (i) incubating cells which express GFRα1 receptor, but not Ret receptor, with a test compound (ii) determining whether an increase in intracellular $Ca^{2+}$ concentration is effected in said cells as compared to controls not incubated with said compound, thereby identifying a compound which is an agonist of GFRα1-dependent, Ret-independent intracellular signaling.

50. The method of claim 49 further comprising determining that said test compound binds to GFRα1 receptors.

51. The method of claim 49, wherein said cells are DRG Ret (−/−) neurons.

52. The method of claim 49, wherein said cells are transformed cells.

53. The method of claim 49, wherein said cells are neuroblastoma cells.

54. A method for identifying a compound which is an antagonist of GFRα1-dependent, Ret-independent intracellular signaling comprising (i) incubating cells which express GFRα1 receptors, but not Ret receptors, with a compound to be tested in the presence of a sufficient amount of an agonist of GFRα1-dependent, Ret-independent intracellular signaling to cause an increase in intracellular $Ca^{2+}$ concentration, and (ii) determining whether a decrease in intracellular $Ca^{2+}$ concentration is effected, as compared with controls performed without said compound to be tested, thereby identifying a compound which is an antagonist of GFRα1-dependent, Ret-independent intracellular signaling.

55. The method of claim 54, wherein said agonist is GDNF.

56. The method of claim 54, wherein said cells are DRG Ret (−/−) neurons.

57. The method of claim 54, wherein said cells are transformed cells.

58. The method of claim 54, wherein said cells are neuroblastoma cells.

59. A method for identifying a compound which is an agonist of GFRα1-dependent, Ret-independent intracellular signaling comprising (i) incubating cells which express GFRα1, but not Ret, with the compound to be tested, (ii) preparing a cell lysate, (iii) immunoprecipitating the detergent insoluble fraction of the cell lysate with anti-GFRα1 antibodies to form an imnmunoprecipitate, and (iv) performing an assay for measuring kinase phosphorylation on said immunoprecipitate, thereby identifying a compound which is an agonist of GFRα1-dependent, Ret-independent intracellular signaling.

60. The method of claim 59, wherein said cells are DRG Ret (−/−) neurons.

61. The method of claim 59, wherein said cells are transformed cells.

62. The method of claim 59 wherein said cells are neuroblastoma cells.

63. A method for identifying a compound which is an antagonist of the GFRα1-dependent, Ret-independent intracellular signaling comprising (i) incubating cells which express GFRα1, but not Ret, with the compound to be tested in the presence of a sufficient amount of an agonist of said intracellular signaling to effect kinase phosphorylation ii) preparing a cell lysate, (iii) immunoprecipitating the detergent insoluble fraction of the cell lysate with anti-GFRα1 antibodies to form an immunoprecipitate, (iv) performing an assay for measuring kinase phosphorylation on said immunoprecipitate, and (v) comparing the results of said assay to those achieved in control experiments performed in the absence of said compound to be tested, thereby identifying a compound which is an antagonist of the GFRα1-dependent Ret-independent intracellular signaling.

64. The method of claim 63 wherein said agonist is GDNF.

65. The method of claim 63, wherein said cells are DRG Ret (−/−) neurons.

66. The method of claim 63, wherein said cells are transformed cells.

67. The method of claim 63, wherein said cells are neuroblastoma cells.

68. A method for identifying a compound which is an agonist of GFRα1-independent, Ret-independent intracellular signaling comprising (i) incubating cells which express GFRα1, but not Ret, with a compound to be tested, and (ii) determining whether activation of Src-type kinase is effected, as compared with controls not incubated with said compound, thereby identifying a compound which is an agonist of GFRα1-dependent, Ret-independent intracellular signaling.

69. The method of claim 68, wherein the Src-type kinase is selected from the group consisting of Fyn, c-Src, and Yes.

70. The method of claim 68, wherein Src-type kinase activation is determined by measuring phosphorylation of MAPK.

71. The method of claim 68, wherein Src-type kinase activation is determined by measuring phosphorylation of CREB.

72. The method of claim 68, wherein said cells are DRG Ret (−/−) neurons.

73. The method of claim 68, wherein said cells are transformed cells.

74. The method of claims 68, wherein said cells are neuroblastoma cells.

75. A method for identifying a compound which is an antagonist of the GFRα1-dependent, Ret-independent intracellular signaling pathway comprising (i) incubating cells which express GFRα1, but not Ret, with a compound to be tested in the presence of a sufficient amount of an agonist of said pathway to cause activation of Src-type kinase and (ii) determining whether said compound effects a decrease in Src-type kinase activation, as compared with controls not incubated with said compound, thereby identifying a compound which is an antagonist of the GFRα1-dependent, Ret-independent intracellular signaling pathway.

76. The method of claim 75 wherein the Src-type kinase is selected from the group consisting of Fyn, c-Src and Yes.

77. The method of claim 75, wherein Src-type kinase activation is determined by measuring phosphorylation of MAPK.

78. The method of claim 75, wherein Src-type kinase activation is determined by measuring phosphorylation of CREB.

79. The method of claim 75, wherein said agonist is GDNF.

80. The method of claim 75, wherein said cells are DRG Ret (−/−) neurons.

81. The method of claim 75, wherein said cells are transformed cells.

82. The method of claim 75, wherein said cells arc neuroblastoma cells.

83. A method for identifying a compound which is an agonist of Ret-independent intracellular signaling effected by GFRα receptors comprising (i) incubating lipid rafts prepared from cells having GFRα receptors with said compound and (ii) determining whether Src-type kinase is activated as compared to controls not incubated with said compound, thereby identifying a compound which is an agonist of Ret-independent intracellular signaling effected by GFRα receptors.

84. The method of claim 83 wherein the Src-type kinase is selected from the group consisting of Fyn, c-Src and Yes.

85. The method of claim 83, wherein Src-type kinase activation is determined by measuring phosphorylation of MAPK.

86. The method of claim 83, wherein Src-type kinase activation is determined by measuring phosphorylation of CREB.

87. A method for identifying a compound which is an antagonist of Ret-independent intracellular signaling effected by GFRα receptors comprising (i) incubating lipid rafts prepared from cells having GFRα receptors with said compound in the presence of a sufficient amount of an agonist of the GFRα-dependent, Ret-independent intracellular signaling pathway to activate Src-type kinases and (ii) comparing the results to control experiments performed in the absence of said compound, thereby identifying a compound which is an antagonist of Ret-independent intracellular signaling effected by GFRα receptors.

88. The method of claim 87 wherein the Src-type kinase is selected from the group consisting of Fyn, c-Src and Yes.

89. The method of claim 87, wherein Src-type kinase activation is determined by measuring phosphorylation of MAPK.

90. The method of claim 87, wherein Src-type kinase activation is determined by measuring phosphorylation of CREB.

91. The method of claim 87, wherein said agonist is GDNF.

* * * * *